United States Patent [19]

Kam et al.

[11] Patent Number: 4,810,717
[45] Date of Patent: Mar. 7, 1989

[54] 2-HYDROXYPROPYLAMINE ARYL ESTER DERIVATIVES

[75] Inventors: Sheung T. Kam, Vernon Hills; William L. Matier, Libertyville, both of Ill.

[73] Assignee: E. I. du Pont de Nemours and Company, Wilmington, Del.

[21] Appl. No.: 838,082

[22] Filed: Mar. 10, 1986

Related U.S. Application Data

[62] Division of Ser. No. 320,773, Nov. 12, 1981, Pat. No. 4,582,855.

[51] Int. Cl.$^4$ .................. C07D 233/66; C07D 263/48; C07D 209/44; C07D 335/02
[52] U.S. Cl. .................................... 514/377; 548/337; 548/233; 548/471; 549/28; 514/398; 514/415; 514/432
[58] Field of Search .................. 548/337, 233, 471; 549/28; 514/398, 377, 415, 432

[56] References Cited

U.S. PATENT DOCUMENTS 4,333,946  6/1982  Durant et al. ..................... 548/337

Primary Examiner—Mary C. Lee
Assistant Examiner—Robert C. Whittenbaugh
Attorney, Agent, or Firm—Gildo E. Fato

[57] ABSTRACT

Novel compounds of the general formula

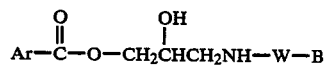

wherein Ar represents a substituted or unsubstituted aromatic or heterocyclic group; W represents alkylene of from 1 to about 10 carbon atoms; and B represents $-NR_2COR_1$, $-NR_2CONR_1R_3$, $-NR_2SO_2R_1$, $-NR_2SO_2NR_1R_3$, or $-NR_2COOR_1$ wherein $R_1$, $R_2$ and $R_3$ may be the same or different and may be hydrogen, alkyl, alkoxyalkyl, cycloalkyl, alkenyl, alkynyl, aryl, heteroaryl, or aralkyl, except that $R_1$ is not hydrogen when B is $-NR_2SO_2R_1$ or $-NR_2COOR_1$, or $R_1$ and $R_3$ may together with N form a 5 to 7 membered heterocyclic group; and the pharmaceutically acceptable salts thereof. These compounds exhibit $\beta$-adrenergic blocking activity and are also useful in the treatment of glaucoma.

33 Claims, No Drawings

2-HYDROXYPROPYLAMINE ARYL ESTER DERIVATIVES

This application is a division of application Ser. No. 320,773, filed Nov. 12, 1981, now U.S. Pat. No. 4,582,855.

BACKGROUND OF THE INVENTION

Compounds of the present invention are useful because of their valuable pharmaceutical properties. They exhibit β-adrenergic blocking activity and are also useful in the treatment of glaucoma.

The present invention also relates to the treatment or prophylaxis of cardiac disorders. More particularly, the invention relates to a novel method of treatment or prophylaxis of cardiac disorders which comprises administration of β-adrenergic blocking agents and to compounds useful in such method.

The therapeutic and prophylactic uses of compounds which block sympathetic nervous stimulation of β-adrenergic receptors in the heart, lungs, vascular system and other organs are well documented. Typically, such compounds are administered therapeutically to patients suffering from ischemic heart disease or myocardial infarction for the purpose of reducing heart work, i.e., heart rate and contractile force. Reducing heart work reduces oxygen demand, and may also actually increase oxygen supply. Thus reducing heart work can aid in the prevention of further tissue damage and can relieve angina pectoris.

β-Adrenergic stimulation may also aggravate or cause arrhythmias because of increased levels of catecholamines. Thus β-blocking agents may be employed to reduce the risks of arrhythmias.

Some of the compounds of the present invention selectively block β-adrenergic receptors in various organs. β-receptors in the heart are generally referred to as $β_1$ receptors, and those associated with vasodilation and bronchodilation are $β_2$ receptors. Selective β-blockers are preferred for the treatment of cardiac disorders, because they may have less potential to cause hypertension or broncho-constriction. A number of $β_1$ selective adrenergic blocking agents have been discovered [Smith, L. H., *J. Appl. Chem. Biotechnol.*, 28, 201–202 (1978)]. Most such compounds are structural variations of 1-amino-3-aryloxy-2-propanol.

Heretofore, the emphasis in β-blocker research has been to develop compounds which can be administered to cardiac patients over long periods of time. However, often it is desirable in the critical care setting to quickly reduce heart work or improve rhythmicity during a cardiac crisis, e.g., during or shortly after a myocardial infarction. Conventional β-blocking agents can be employed for such treatment, but their duration of action may be much longer than desired by the physician. A β-blocking agent possessing a long duration of action does not allow precise control of heart work or prompt reversal of the β-blocking effect, which may be required in a critical care setting. For instance, if heart output becomes dangerously low, it is desirable to quickly reduce or eliminate β-blocking activity. The lingering activity of available β-blocking agents can be counterproductive and can greatly complicate the therapeutic decisions required of the physician during such critical care of cardiac patients.

Accordingly, there is a need for a pharmaceutical preparation and method of treatment, employing a β-adrenergic blocking agent having a short duration of action.

Compounds of the present invention are novel β-blocking agents. The presence of the ester function in these compounds provides for predictable metabolism of these compounds to metabolites which are inactive as β-blockers and are highly polar and readily excreted.

Some of the compounds of the present invention are metabolized rapidly after infusion into the systemic circulation and, therefore, have a short duration of β-blocking action. Such compounds are particularly advantageous since they allow precise control during treatment of certain cardiovascular diseases by intravenous administration of the compound.

Compounds of the present invention are also useful for the treatment of glaucoma or lowering of intraocular pressure by topical administration of the compounds to the eye. Compounds with short duration in the systemic circulation, but with good stability in ocular fluid, are particularly useful since they have a low potential for producing systemic side effects.

Glaucoma is a condition of the eye characterized by increased intraocular pressure. Untreated, the condition can eventually lead to irreversible retinal damage and blindness. Conventional therapy for glaucoma has involved topical administration of pilocarpine and/or epinephrine, administered to the eye several times daily.

The use of various β-blocking agents to lower intraocular pressure is well documented. For example, U.S. Pat. No. 4,195,085 to Stone discloses a method for treatment of glaucoma by the optical administration of a β-blocking compound, timolol maleate. U.S. Pat. No. 4,127,674 discloses a method of treating glaucoma with labetalol, a known antagonist of both alpha and beta adrenergic receptors. However, these methods also possess significant drawbacks, in that the absorption of the β-blocking compound into the systemic circulation can cause undesirable side effects. Such side effects result from prolonged β-blocking action on the heart, bronchioles and blood vessels. For example, according to *Physicians' Desk Reference*, Charles E. Baker, Jr., 35th Edition, 1981, p. 1233, adverse reactions to the topical use of timolol maleate can include broncho-spasm and heart failure, as well as cardia conduction defects. Accordingly, there is a need for a method of treatment for glaucoma or for lowering intraocular pressure which is relatively free of unwanted systemic side-effects.

SUMMARY OF THE INVENTION

The present invention relates to compounds of the general formula

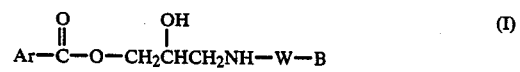

$$Ar-\overset{O}{\underset{\|}{C}}-O-CH_2\overset{OH}{\underset{|}{CH}}CH_2NH-W-B \qquad (I)$$

wherein Ar represents a substituted or unsubstituted aromatic group or heterocyclic group; W represents alkylene of from 1 to about 10 carbon atoms; and B represents $-NR_2COR_1$, $-NR_2CONR_1R_3$, $-NR_2SO_2R_1$, $NR_2SO_2NR_1R_3$, or $-NR_2COOR_1$ wherein $R_1$, $R_2$ and $R_3$ may be alike or different and may be hydrogen, alkyl, alkoxyalkyl cycloalkyl, alkenyl, alkynyl, aryl, heteroaryl, or aralkyl, except that $R_1$ is not hydrogen when B is $-NR_2SO_2R_1$ or $-NR_2COOR_1$, or $R_1$ and $R_3$ may together with N form a 5 to 7 membered heterocyclic group and the pharmaceutically acceptable salts thereof.

DETAILED DESCRIPTION OF THE INVENTION

The present invention relates to compounds of the formula

wherein Ar represents a substituted or unsubstituted aromatic group, including monocyclic, polycyclic and heterocyclic ring systems; W represents a straight or branched chain alkylene of from 1 to about 10 carbon atoms; and B represents —NR$_2$COR$_1$, —NR$_2$CONR$_1$R$_3$, —NR$_2$SO$_2$R$_1$, —NR$_2$SO$_2$NR$_1$R$_3$, or —NR$_2$COOR, wherein R$_1$, R$_2$ and R$_3$ may be the same or different and may be hydrogen, alkyl, of from 1 to about 10 carbon atoms, alkoxyalkyl wherein the alkyl groups may be the same or different and contain from 1 to about 10 carbon atoms, cycloalkyl of from 3 to about 8 carbon atoms, alkenyl of from 3 to about 10 carbon atoms, alkynyl of from 3 to about 10 carbon atoms, aryl which includes monocyclic or polycyclic aromatic or heterocyclic ring systems of from 2 to about 10 carbon atoms such as phenyl, thiophenyl, imidazole, oxazole, indole, and the like, aralkyl wherein the alkyl group contains from about 1 to about 6 carbon atoms and the aryl group represents substituted or unsubstituted monocyclic or polycyclic aromatic or heterocyclic ring systems of from 2 to about 10 carbon atoms, such as benzyl, phenethyl, 3,4-dimethoxyphenethyl, 1,1-dimethyl-2-(3-indolyl)ethyl and the like, except that R$_1$ is not hydrogen when B is —NR$_2$SO$_2$R$_1$ or —NR$_2$COOR$_1$, or R$_1$ and R$_3$ may together with N form a 5 to 7 membered heterocyclic group, such as pyrrolidine, piperidine, piperazine, morpholine or thiomorpholine. Aromatic (Ar) substituents may include lower alkyl of from 1 to about 10 carbon atoms, alkenyl of from 2 to about 10 carbon atoms, alkynyl of from 2 to about 10 carbon atoms, alkoxy wherein the alkyl group contains from 1 to about 10 carbon atoms, halogen, acetamido, amino, nitro, alkylamino of from 1 to about 10 carbon atoms, hydroxy, hydroxyalkyl of from 1 to about 10 carbon atoms, cyano, arylalkoxy wherein the alkyl group contains from 1 to about 6 carbon atoms and the aryl group represents substituted or unsubstituted phenyl and groups of the formula

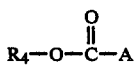

wherein R$_4$ is lower alkyl, aryl or aralkyl and A is a direct bond, alkylene of from 1 to about 10 carbon atoms or alkenylene of from 2 to about 10 carbon atoms. The compounds described herein are not limited to any particular stereoisomeric configuration. Such compounds may be administered as their pharmaceutically acceptable acid addition salts, e.g., as the hydrochloride, sulfate, phosphate, gluconate, tartrate, etc.

Included in the present invention are compounds of the formula

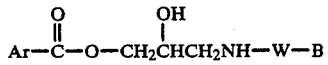

wherein Ar represents an aromatic group which may be unsubstituted or substituted with alkyl of from 1 to about 6 carbon atoms, alkenyl of from 2 to about 6 carbon atoms, alkynyl of from 2 to about 10 carbon atoms, alkoxy wherein the alkyl group contains from 1 to about 6 carbon atoms, halogen, acetamido, amino, nitro, alkylamino of from 1 to about 6 carbon atoms, hydroxy, hydroxyalkyl of from 1 to about 6 carbon atoms, cyano or arylalkoxy wherein the alkyl group contains from 1 to about 6 carbon atoms and the aryl group is substituted or unsubstituted phenyl; W represents alkylene of from 1 to about 10 carbon atoms; and B represents —NR$_2$COR$_1$, —NR$_2$CONR$_1$R$_3$, —NR$_2$SO$_2$R$_1$, —NR$_2$SO$_2$NR$_1$R$_3$, or —NR$_2$COOR$_1$ wherein R$_1$, R$_2$ and R$_3$ may be the same or different and represent hydrogen, alkyl of from 1 to about 6 carbon atoms, alkoxyalkyl wherein the alkyl groups may the same or different and contain from 1 to about 6 carbon atoms, cycloalkyl of from 3 to about 8 carbon atoms, alkenyl of from 2 to about 6 carbon atoms, alkynyl of from 2 to about 6 carbon atoms, aralkyl wherein the alkyl group contains from 1 to about 6 carbon atoms and the aryl group represents substituted or unsubstituted monocyclic or polycyclic aromatic or heterocyclic ring systems of from 2 to about 10 carbon atoms, or a substituted or unsubstituted aromatic or heterocyclic group of from 2 to about 10 carbon atoms wherein the substitutent groups may be alkyl of from 1 to about 6 carbon atoms, except that R$_1$ is not hydrogen when B is —NR$_2$SO$_2$R$_1$ or —NR$_2$COOR$_1$, or R$_1$ and R$_3$ may together with N form a 5 to 7 membered heterocyclic group; and the pharmaceutically acceptable salts thereof.

The present invention also includes compounds of the formula

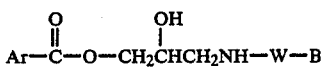

wherein Ar represents phenyl which is unsubstituted or substituted with alkyl of from 1 to about 6 carbon atoms, alkoxy wherein the alkyl group contains from 1 to about 4 carbon atoms, halogen, hydroxy, nitro, amino, phenoxy, or benzyloxy; W represents alkylene of from 1 to about 6 carbon atoms; and B represents —NR$_2$COR$_1$, —NR$_2$CONR$_1$R$_3$, —NR$_2$SO$_2$R$_1$, —NR$_2$SO$_2$NR$_1$R$_3$, or NR$_2$COOR$_1$, wherein R$_1$, R$_2$ and R$_3$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, a substituted or unsubstituted aryl group of from 5 to about 6 carbon atoms, or a 5 to 7 membered heterocyclic group, except that R$_1$ is not hydrogen when B is —NR$_2$SO$_2$R$_1$ or —NR$_2$COOR$_1$, or R$_1$ and R$_3$ may together with N form a 5 to 7 membered heterocyclic group; and the pharmaceutically acceptable salts thereof.

Additionally the present invention includes compounds of the formula

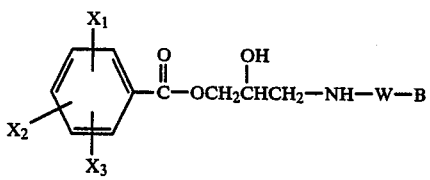

wherein $X_1$, $X_2$ and $X_3$ may be the same or different and represent hydrogen, halogen, hydroxy, hydroxyalkyl of from 1 to about 6 carbon atoms, nitro, amino, alkyl of from 1 to about 6 carbon atoms, phenoxy benzyloxy, or alkoxy wherein the alkyl group contains from 1 to about 4 carbon atoms; W represents alkylene of from 1 to about 6 carbon atoms; and B represents —NR$_2$COR$_1$, —NR$_2$CONR$_1$R$_3$, —NR$_2$SO$_2$R$_1$, —NR$_2$SO$_2$NR$_1$R$_3$, or —NR$_2$COOR$_1$ wherein R$_1$, R$_2$, and R$_3$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, phenyl benzyl, or a 5 to 7 membered heterocyclic group, except that R$_1$ is not hydrogen when B is —NR$_2$SO$_2$R$_1$ or —NR$_2$COOR$_1$, or R$_1$ and R$_3$ may together with N form a 5 to 7 membered heterocyclic group; and the pharmaceutically acceptable salts thereof.

Preferred compounds of the present invention are compounds of the formula

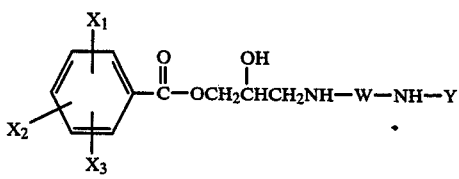

wherein $X_1$, $X_2$ and $X_3$ may be the same or different and represent hydrogen, halogen, hydroxy, hydroxyalkyl of from 1 to about 6 carbon atoms, nitro, amino, benzyloxy, phenoxy, alkyl containing from 1 to about 6 carbon atoms, or alkoxy wherein the alkyl group contains from 1 to about 6 carbon atoms; W represents ethylene, 1-methylethylene, or 1,1-dimethylethylene, and Y is —COR$_1$, —CONR$_1$R$_3$, —SO$_2$R$_1$, —SO$_2$NR$_1$R$_3$, or —COOR$_1$, wherein R$_1$ and R$_3$ may be the same or different and may be hydrogen, alkyl containing from 1 to about 6 carbon atoms, alkoxyalkyl wherein the alkyl groups may be the same or different and contain from 1 to about 6 carbon atoms, substituted or unsubstituted phenyl, substituted or unsubstituted heterocyclic group of from 2 to about 10 carbon atoms, aralkyl wherein the alkyl group contains from 1 to about 6 carbon atoms and the aryl group represents substituted or unsubstituted phenyl, or a heterocyclic group of from 2 to about 10 carbon atoms, except that R$_1$ is not hydrogen when Y is —SO$_2$R$_1$ or COOR$_1$, or R$_1$ and R$_3$ may together with N form a 5 to 7 membered heterocyclic group; and the pharmaceutically acceptable salts thereof.

Particularly preferred compounds are compounds of the following formulae

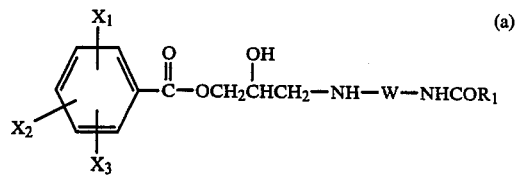

wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and R$_1$ represents alkyl of from 1 to about 6 carbon atoms, alkoxyalkyl wherein the alkyl groups may the same or different and contain from 1 to about 4 carbon atoms, cycloalkyl of from 3 to about 8 carbon atoms, phenyl, benzyl, or a 5 to 7 membered heterocyclic group; and the pharmaceutically acceptable salts thereof.

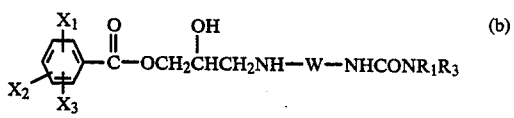

wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and R$_1$ and R$_3$ may be the same or different and represent hydrogen, alkyl of from 1 to about 6 carbon atoms, alkoxyalkyl wherein the alkyl groups may be the same or different and contain from 1 to about 4 carbon atoms, cycloalkyl of from 3 to about 8 carbon atoms, phenyl, or benzyl, or R$_1$ and R$_3$ may together with N form a 5 to 7 membered heterocyclic group; and the pharmaceutically acceptable salts thereof.

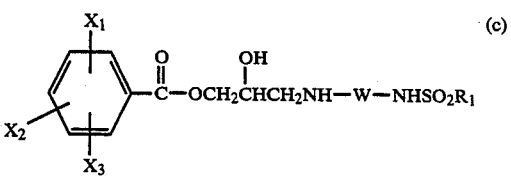

wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and R$_1$ represents alkyl of from 1 to about 6 carbon atoms, alkoxyalkyl wherein the alkyl groups may be the same or different and contain from 1 to about 4 carbon atoms, cycloalkyl of from 3 to about 8 carbon atoms, phenyl, benzyl, or a 5 to 7 membered heterocyclic group; and the pharmaceutically acceptable salts thereof.

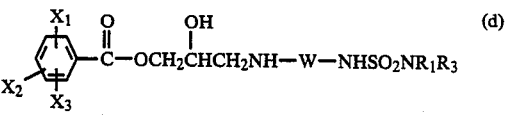

wherein $X_1$, $X_2$ and $X_3$ may be the same or different and represent hydrogen, halogen, hydroxy, nitro, amino, alkyl of from 1 to about 4 carbon atoms, or benzyloxy;

W represents alkylene of from 1 to about 6 carbon atoms; and $R_1$ and $R_3$ may be the same or different and represent hydrogen, alkyl of from 1 to about 6 carbon atoms, alkoxyalkyl wherein the alkyl groups may be the same or different and contain from 1 to about 4 carbon atoms, cycloalkyl of from 3 to about 8 carbon toms, phenyl, benzyl, or $R_1$ and $R_3$ may together with N form a 5 to 7 membered heterocyclic group; and the pharmaceutically acceptable salts thereof.

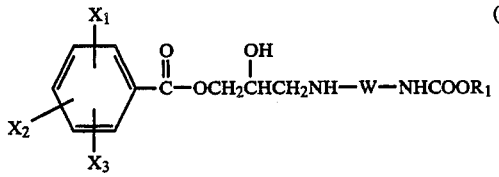
(e)

wherein $X_1$, $X_2$ and $X_3$ may be the same or different and represent hydrogen, halogen, hydroxy, nitro, amino, alkyl of from 1 to about 4 carbon atoms, or benzyloxy; W represents alkylene of from 1 to about 6 carbon atoms; and $R_1$ represents alkyl of from 1 to about 6 carbon atoms, alkoxyalkyl wherein the alkyl groups may be the same or different and contain from 1 to about 4 carbon atoms, and the pharmaceutically acceptable salts thereof.

Compounds of the present invention exist as two sterioisomers due to the presence of an asymmetric carbon atom. The present invention includes either stereoisomeric form as well as racemic mixtures. For compounds in which $R_1$, $R_2$ or $R_3$ represent alkenyl, both cis and trans isomers are within the scope of the invention. For compounds in which Ar is a substituted aromatic ring, the substituents may be in the ortho, meta or para positions to the propoxy carbonyl side-chain.

The compounds described herein may be prepared by any available procedure. Compounds prepared as the acid addition salts may be converted to the free base by reaction with an appropriate base such as sodium carbonate or sodium bicarbonate. The compounds are advantageously prepared by one of the following methods:

(1) As shown in Scheme I, an appropriate acyl chloride is reacted with glycidol in the presence of a base such as pyridine. The resulting product is then reacted with an appropriate amine in the presence of dimethylformamide:

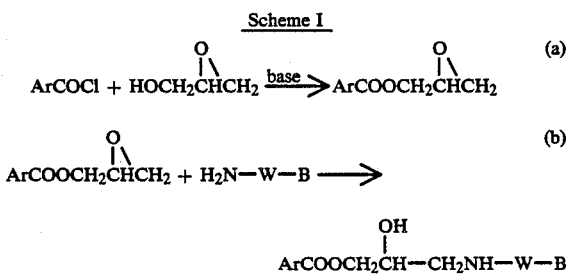

where Ar, W and B are defined as hereinbefore.

(2) As shown in Scheme II, an appropriate amine is reacted with glycidol. The resulting amino-diol is reacted with an acyl chloride.

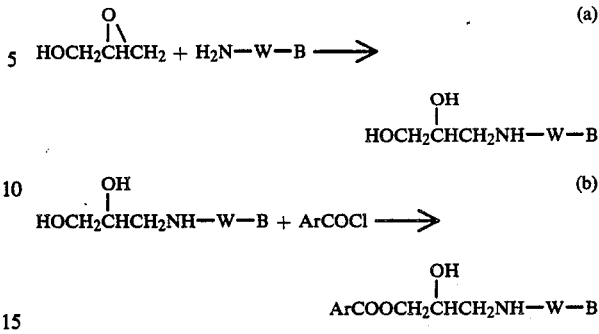

wherein Ar, W, and B are defined as hereinbefore.

Alternatively, as shown in Scheme III, the amino-diol is reacted with p-methoxybenzyloxycarbonyl azide in the presence of sodium bicarbonate and dioxane to protect the amine group. The resulting compound is reacted with an appropriate acyl chloride and the protecting group is removed by reaction with a suitable acid.

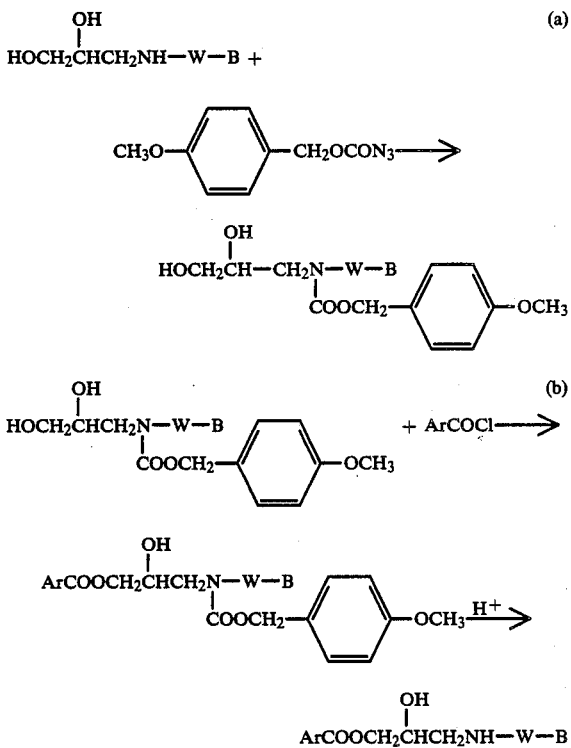

wherein Ar, W and B are defined as hereinbefore.

The acyl chlorides used as starting materials in the above reaction schemes are generally commercially available compounds or may be prepared by methods known in the art.

The amines, $H_2N-W-B$, wherein W and B are defined as hereinbefore, may be prepared by the following methods:

(a) For amidoalkylamines (B=$NR_2COR_1$):

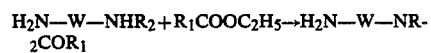

wherein W, $R_2$ and $R_1$ are defined as hereinbefore.

(b) For alkoxycarbonylaminoalkyl amines ($B=NR_2COOR_1$), either of two methods were used.

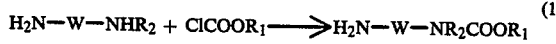  (1)

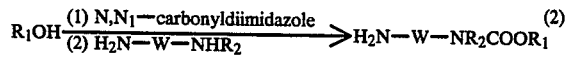  (2)

wherein W, $R_2$ and $R_1$ are defined as hereinbefore.

(c) For ureidoalkylamines ($B=NR_2CONR_1R_3$) any of four methods were used:

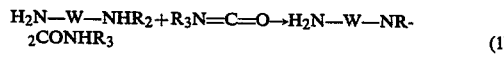  (1)

wherein W, $R_2$ and $R_3$ are defined as hereinbefore.

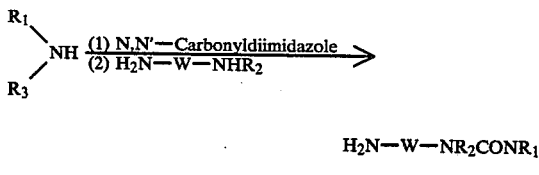  (2)

wherein W, $R_1$, $R_2$ and $R_3$ are defined as hereinbefore.

  (3)

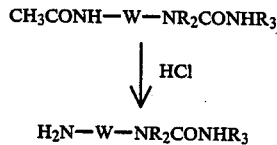

wherein W, $R_2$ and $R_3$ are defined as hereinbefore.

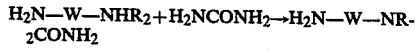  (4)

wherein W and $R_2$ are defined as hereinbefore.

(d) For sulfonamidoalkylamines ($B=NR_2SO_2R_3$):

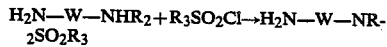

wherein W, $R_2$ and $R_3$ are defined as hereinbefore.

(e) For sulfamidoalkylamines ($B=NR_2SO_2NR_1R_3$), either of two methods were used:

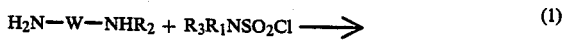  (1)

  (2)

wherein W, $R_1$, $R_2$ and $R_3$ are defined as hereinbefore.

The preparation of some of the starting materials is described in copending U.S. Application Ser. No. 211,341 which is hereby incorporated by reference.

When used for the treatment of cardiac disorders, compounds of this invention are advantageously administered orally or parenterally, e.g., by intravenous injection or intravenous infusion. Formulations for intravenous injection preferably include the active compound as a soluble acid addition salt in a properly buffered isotonic solution.

The dosage administered to a patient and the duration of infusion will depend upon the patient's needs and the particular compounds employed. For short periods of infusion, e.g., less than about three hours, the duration of effect is thought to be determined by both metabolic effects and distribution phenomena. For relatively long periods of infusion, e.g., greater than about three hours, the duration of effect is thought to depend largely on metabolic effects. Accordingly, although the present methods and compounds are generally useful for short-term infusion therapy, certain compounds are preferred for longer durations of infusion. The compounds have been found to be generally non-toxic within conventional dosage ranges. Dosages of about 0.0001 to about 100 mg. per kg. of body weight per hour are generally employed, with preferred dosages ranging from about 0.01 to about 10 mg. per kg. of body weight per hour.

When used for the treatment of glaucoma, the compounds of this invention are advantageously administered topically to the eye in the form of a solution, ointment or solid insert such as is described in U.S. Pat. No. 4,195,085. Formulations may contain the active compound, preferably in the form of a soluble acid addition salt, in amounts ranging from about 0.01 to about 10% by weight, preferably from about 0.5 to about 5% by wt. Unit dosages of the active compound can range from about 0.001 to about 5.0 mg., preferably from about 0.05 to about 2.0 mg. The dosage administered to a patient will depend upon the patient's needs and the particular compounds employed.

Carriers used in the preparations of the present invention are preferably non-toxic pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. The pharmaceutical preparations may also contain additional components such as emulsifying, preserving, wetting and sterilizing agents. These include polyethylene glycols 200, 300, 400 and 600, carbowaxes 1,000, 1,500, 4,000, 6,000 and 10,000, bacteriocidal components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose, including conventional phosphate buffer vehicle systems, isotonic boric acid vehicles, isotonic sodium chloride vehicles, isotonic sodium borate vehicles and the like.

The method of treatment of this invention advantageously involves the topical administration of eye drops containing the active compound. Formulations for eye drops preferably include the active compound as a soluble acid addition salt in a properly buffered, sterile, aqueous isotonic solution.

The compounds of the present invention are ester group-containing beta blockers that have a selective, localized, β-blocking effect in the eye after topical administration. Such compounds are thought to be rapidly metabolized by plasma and/or liver esterases into inactive by-products, upon entering the systemic circulation. It has been discovered that these same compounds are relatively stable in ocular fluids, i.e., lacrimal fluids and aqueous humor. Consequently, such compounds are useful for the treatment of glaucoma or for lowering intraocular pressure since they remain stable when topically applied to the eye but rapidly metabolize when subsequently absorbed into the systemic circulation.

Some of the compounds break down in the aqueous humor more rapidly than others. Such compounds may advantageously be employed when only a temporary reduction in intraocular pressure is desired, say for diagnostic procedures. Longer-acting compounds are generally used for effecting longer-term reductions in intraocular pressure, such as is desired when treating chronic glaucoma. Thus, the method of the present invention provides a very useful therapeutic alternative for the treatment of glaucoma or for lowering intraocular pressure.

The rate of hydrolysis of the ester function of compounds of the present invention is influenced by the type of amine substituent. By varying the amine substituent it is possible to vary the length of duration of the compound in the body. The presence of the amine substituent also makes the compounds less lipophilic. Compounds that are less lipophilic have a reduced potential to cause central nervous system effects since there is less potential for CNS penetration.

The in vitro studies hereinafter described indicate that the compounds used in the method of the present invention will undergo different rates of enzymatic hydrolysis depending on their location within the body (see Table III). For example, the compound of Example VII is completely hydrolyzed within 60 minutes in both dog blood and liver homogenate while only 31% hydrolyzed after one hour in aqueous humor, and only 54% hydrolyzed after two hours. The compound of Example II is less stable in aqueous humor, hydrolyzing 42% after one hour, 68% after two hours.

The beta adrenergic receptor blocking activity of several compounds of the present invention has been demonstrated in vitro (Table I) and in vivo (Table II).

A. Beta Blocking Activity In Vitro

Several of the compounds of the present invention were tested for β-blocking activity in vitro using guinea pig right atria and guinea pig tracheal strips mounted in a tissue bath containing oxygenated (95% $O_2$-5% $CO_2$) Krebs physiological salt solution at 37° C. Each tissue was suspended between a fixed glass rod and a Statham Universal Transducer connected to a Beckman recorder. Atria were allowed to beat spontaneously under a loading tension of approximately 0.5 gm. Intrinsic depressant or stimulant activity was determined for each compound by progressively increasing concentrations in the tissue baths at 60-minute intervals. Tissues were not washed between increments. The maximum concentration showing little or no cardiodepressant activity was chosen for blockade experiments. Changes in rate in response to isoproterenol, a standard β-receptor agonist, were measured in the absence and presence of test compounds. Spiral strips of guinea pig trachea were suspended under 5 gm resting tension and incubated with phentolamine, tropolane and cocaine. Active tension was generated by addition of carbachol $(3.0 \times 10^{-7}M)$ and decreases in tension in response to isoproterenol were quantitated. Cumulative concentration-response curves were produced with isoproterenol both before and after 60-minute incubation of test compounds with atria and trachea. Compounds with β-blocking activity shifted concentration-response curves to the right. The blocking potency of test compounds was estimated by computing $pA_2$ values ($-\log K_8$) by the method of Furchgott, the Pharmacological Differentiation of Adrenergic Receptors, Ann. N.Y. Acad. Sci., 139: 553–570 (1967). Comparison of blockade of right atrial and tracheal responses to isoproterenol permits assessment of cardioselectivity of test compounds; i.e., cardioselective compounds are relatively more effective in blocking atrial rate than tracheal force response to isoproterenol. The degree of cardioselectivity was estimated from the ratio, $K_B$ trachea/$K_B$ atria $(10^{(pA2atria-pA2trachea)})$. A ratio greater than one indicates cardioselectivity. Test drugs were dissolved in distilled water and added to the bath (30 ml) in a volume of 10 or 100 μl. The results of the in vitro tests are contained in Table I. All of the test compounds are active β-blockers.

TABLE I

| Compound of Example | Beta-Blocking Activity In Vitro | | Cardioselectivity $K_B$(Trachea)/$K_B$(Atria) |
|---|---|---|---|
| | $PA_2$ | | |
| | Rt. Atria | Trachea | |
| I | 6.1 | | |
| II | 8.5 | 8.2 | 2 |
| III | <6.3 | | |
| IV | 7.5 | 8.0 | −3 |
| V | 6.8 | 8.1 | −18 |
| VI | 7.7 | 7.2 | −3 |
| VII | 7.4 | 8.1 | −5 |
| VIII | 7.0 | 6.9 | 0 |
| IX | 7.1 | 7.1 | 0 |
| X | 7.7 | 7.9 | −2 |
| XI | 6.5 | 8.1 | −39 |
| XII | 7.1 | 6.4 | 5 |
| XIII | <6.0 | | |
| XXXI | 7.7 | 7.7 | 0 |
| XXXII | 7.4 | 7.5 | 0 |
| XXXIII | 8.3 | | |
| XXXIV | 7.9 | | |
| XXXV | 8.2 | 8.6 | −3 |
| XXXVI | 8.1 | 8.4 | −2 |
| XXXVI | 8.2 | 8.4 | −1 |
| XXXVIII | 9.0 | 8.8 | 1 |
| Propanolol | 8.7 | 8.9 | −1 |

B. Duration and Potency of Beta-Blocking Action in Vivo

The duration of β-blockade was determined in vivo using pentobarbital-anesthetized dogs instrumented for measurement of heart rate using a Beckman cardiotachometer triggered electronically by a phasic aortic blood pressure signal. Both vagus nerves were severed in the cervical region and the animals were mechanically ventilated. The experimental design used employed a 3-hour infusion of test compound. Bolus doses of isoproterenol (0.5 μg/kg) were used to assess the degree of β-blockade and recovery from β-blockade after determination of the infusion. The doses were spaced at 10-minute intervals and were given before, during and following the infusion of test compounds. The infusion rate was adjusted so that at the end of the 3-hour infusion period the degree of isoproterenol inhibition averaged about 50% of control. Following termination of blocker infusion, percent recovery from β-blockade was computed and the time associated with 80% recovery estimated. The results are contained in Table II.

TABLE II

β-Blocking Activity In Vivo

| Compound of Example | Potency (mg/kg/180 min) | % I[a] | Recovery Time (min) 50% | 80% | N[b] |
|---|---|---|---|---|---|
| IV | 2.7 | 61 | 7 | 35 | 2 |
| V | 0.6 | 62 ± 5 | 10 ± 2 | 22 ± 6[c] | 6 |
| VI | 1.4 | 61 | 8 ± 3 | 12 ± 3 | 3 |
| VII | 1.8 | 68 | 8 | 19 | 1 |
| VIII | 10.3/21.9 | 43/55 | 3,4 | 6/36 | 2 |
| IX | 6.5 ± 1.8 | 49 ± 4 | 3 ± 1 | ± 3 | 3 |
| X | 0.7 | 49 | | 21 | 2 |
| XI | 0.2 | 81/71 | | >60 | |
| XXXV | 0.08 | 95 | >60 | >60 | 1 |
| Propanolol | 0.2 | 67 ± 6 | >60 | >60 | 2 |

[a]Percent inhibition of heart rate response to isoproterenol
[b]Number of experiments
[c]2/6 experiments did not recover to 80% within 60 min C. Enzymatic Hydrolysis of Beta Blockers By Dog Blood, Liver Homogenate and Aqueous Humor Chemicals—Acetonitrile was "HPLC" grade. Distilled water was used to dissolve the compounds and 0.01N HCl was used to dissolve compounds requiring an acidic pH for dissolution.

Enzyme Source—Fresh aqueous humor was collected from eyes of dogs using a 23-gauge needle while fresh dog blood was collected into heparinized Vacutainer tubes. Fresh liver was homogenized in 0.9% NaCl using a Potter-Elvehjem Teflon pestle and glass homogenizer making a 25% (W/V) homogenate.

Incubation Condition—A 0.5 ml aliquot of dog aqueous humor, blood or liver homogenate was incubated with 12.5 μg (0.5 ml) of beta blocker in a Dubnoff shaking metabolic incubator at 37° C. for 60 and 120 min. Denatured tissue controls were prepared by adding 2.0 ml of acetonitrile into 0.5 ml of aqueous humor, blood or liver homogenate to destroy esterase activities prior to addition of the beta blockers. These controls were then incubated at 37° C. for 120 min. After 60 and 120 min, the incubations were terminated by addition of 2 ml of acetonitrile and immediately mixed by a Vortex ® to stop esterase activities.

Sample Processing and Data Analyses—All samples were centrifuged at 4000 RPM for 10 min to sediment denatured proteins. The resultant supernatants were transferred to WISP ® vials and analyzed using an HPLC assay developed for beta blockers. The hydrolysis of beta blockers by aqueous humor, blood and liver homogenate was determined by disappearance of the compounds. The extent of enzymatic hydrolysis by each tissue was determined by comparing the amount of each compound (absolute peak area) recovered at each time point to the amount of each compound (absolute peak area) in denatured tissue control and aqueous control samples. The results of these experiments are shown in Table III.

D. Half-Lives of Beta Blockers in Dog Whole Blood and Dog Liver Homogenate

These examples describe experiments which demonstrate the disappearance of the compounds of the present invention in vitro in human whole blood, dog whole blood and dog liver homogenate. The rate of disappearance of a compound is expressed as the half-life ($T_{\frac{1}{2}}$), which is the time period in which one half of the initial amount of compound tested disappears. In each experiment, 1 ml of a solution containing 50 μg of the test compound was added to 1 ml of whole blood or 1 ml of a 33% (w/v) liver homogenate. The samples were incubated in a Dubnoff shaking metabolic incubator for 2.5, 5.0, 10.0, 20.0, 30.0 and 60.0 minutes at 37° C. At the designated time periods, the test mixtures were removed from the incubator and transferred to a 0° C. ice bath. Acetonitrile (2 ml) was immediately added and the mixtures were mixed to stop enzymatic hydrolysis. Zero time samples were prepared by adding 2 ml of acetonitrile to denature the proteins prior to addition of the test compounds. After centrifugation to sediment denatured proteins, 2 ml of the supernatant was removed and analyzed by high pressure liquid chromatography, using a mobile phase of 60% acetonitrile/40% 0.05 m sodium phosphate buffer (pH 6.6), a U.V. detector and Waters u Bondapak Phenyl column. The half life of each test compound was determined graphically by plotting the decrease in concentrations as a function of time. The results of the experiments are shown in Table III.

The present invention is further illustrated by the following examples which are not intended to be limiting.

TABLE III

STABILITY IN DOG BLOOD, LIVER HOMOGENATE AND AQUEOUS HUMOR

| COMPOUND OF EXAMPLE | DOG BLOOD %1 HR[a] | %2 HR[a] | T½ min[b] | DOG LIVER HOMOGENATE %1 HR[a] | %2 HR[a] | T½ min[b] | DOG AQUEOUS HUMOR %1 HR[a] | %2 HR[a] | T½ min[c] |
|---|---|---|---|---|---|---|---|---|---|
| VII | 0 | 0 | 6 | 0 | 0 | 25 | 69 | 46 | 120 |
| V | 12 | 8 | 20 | 0 | 0 | 3.5 | 75 | 49 | 120 |
| IV | 0 | 0 | 7.5 | 39 | 23 | — | 87 | 52 | 120 |
| VIII | 0 | 0 | 15 | 0 | 0 | — | — | — | — |
| II | 0 | 0 | 15 | 0 | 0 | — | 58 | 32 | 60–120 |
| IX | 0 | 0 | 8 | 0 | 0 | 1 | 0 | 0 | 0 |
| X | 0 | 0 | 15 | 0 | 0 | 2.5 | 0 | 0 | 0 |

[a]Percent drug remaining - determined by procedure C.
[b]Half-life determined by procedure D.
[c]Approximate value - determined by procedure C.

EXAMPLE I

This example describes the synthesis of a compound of the following formula via Scheme III:

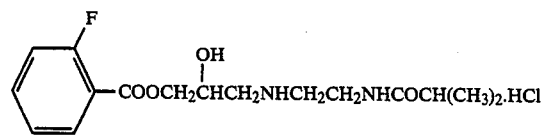

(a) 3-[(2-Isopropylcarbonylamino)ethylamino]1,2-propanediol

To 39 g (0.3 mol) of 2-(isopropylcarbonylamino)ethylamine in 150 ml of isopropyl alcohol was added 22.2 g (0.3 mol) of glycidol. The reaction mixture was stirred at 25° C. for 24 hours and evaporated in vacuo. The residual oil was chromatographed (silica gel/ethanol) to give 18.6 g (30%) of product. This compound was identified by NMR and IR spectroscopy.

(b) 3-[N-(4-Methoxybenzyloxycarbonyl)-N-[(2-isopropylcarbonylamino)ethyl]amino-1,2-propanediol A mixture of 18.6 g (91 mmol) of the 3-[2-(isopropylcarbonylamino)ethylamino]-1,2-propandiol, 20 g (97 mmol) of p-methoxybenzyloxycarbonyl azide and 24 g (280 mmol) of sodium bicarbonate in 66 ml of dioxane and 33 mL of water was stirred at room temperature for 3 days.

The reaction mixture was filtered and the filtrate was evaporated to dryness. The residue was chromatographed, silica gel/10% ethanol in chloroform to give 16 g (47.6%) of product. The compound was identified by NMR and IR spectroscopy.

(c) 2-Hydroxy-3-[N-[4-methoxybenzyloxycarbonyl]-N-[(2-isopropylcarbonylamino)ethyl]]aminopropyl 2-Fluorobenzoate To a mixture containing 8 g (2.2 mmol) of the diol from the previous experiment in 50 ml of methylene chloride-pyridine (1:1) was added 3.5 g (2.2 mmol) of o-fluorobenzoyl chloride at 25° C. The reaction mixture was stirred at 25° C. for 2.5 hours and evaporated to dryness in vacuo at 60° C. The residue was partitioned between water and methylene chloride. The methylene chloride layer was washed with 5% sodium bicarbonate aqueous solution and evaporated to dryness. The product was purified by chromatography; silica gel/10% ethanol in chloroform. The yield was 75% and the compound was identified by NMR and IR spectroscopy.

(d) 3-[2-(Isopropylcarbonylamino)]ethyl]amino-2-hydroxypropyl 2-Fluorobenzoate Hydrochloride Hydrogen chloride gas was passed for 5 minutes into a mixture of 8 g of the ester obtained from the previous experiment in 150 ml of methylene chloride-ethanol (99:1). The reaction mixture was stirred at 25° C. for 3 hours and the precipitate was filtered and recrystallized in isopropanol to give 3.3 g (56%) of product; m.p. 162.5°–163° C. The NMR and IR spectra were consistent with the assigned structure and the elemental analysis was consistent with the empirical formula $C_{16}H_{24}N_2O_4FCl$.

EXAMPLE II

This example describes the synthesis of a compound of the following formula via Method I:

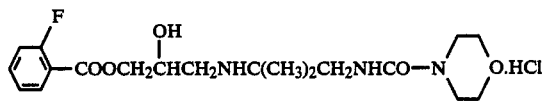

3-[1,1-Dimethyl-2-(1-morpholinocarbonylamino)]ethylamino-2-hydroxypropyl 2-Fluorobenzoate Hydrochloride A mixture containing 37 g (0.5 mol) of glycidol, 500 ml of anhydrous ethyl ether, 500 ml of pyridine and 80 g (0.5 mol) of o-fluorobenzoyl chloride was stirred at 0° C. for 1 hour and 25° C. for 2 hours. The mixture was filtered and the ethanol filtrate was washed with 100 ml of 5% hydrochloric acid. Evaporation of the ethyl ether gave an oil which was distilled to give 69.5 g (71%) of the product, 2,3-epoxypropyl 2-fluorobenzoate, which had a boiling point of 115° C./0.5 mmHg. The NMR and IR spectra were consistent with the assigned structure.

To 8.5 g (0.043 mol) of 2,3-epoxypropyl 2-fluorobenzoate in 100 ml of dimethylformamide was added 8.74 g (0.043 mol) of 1,1-dimethyl-2-(1-morpholinocarbonylamino)ethylamine. The reaction mixture was stirred at 25° C. for 4 hours and the dimethylformamide was evaporated in vacuo at 60° C. The product was purified by column chromatography; silica gel/ethyl ether-ethanol (4:1) to give a colorless oil which was dissolved in ether and acidified with etheral hydrochloric acid. The precipitate was filtered and recrystallized in isopropanol-ethyl ether to give 4.1 g (24%) of product; melting point 58.5°–59.5° C. The NMR and IR spectra were consistent with the assigned structure and elemental analysis was consistent with the empirical formula $C_{19}H_{29}N_3O_5FCl$.

EXAMPLE III

This example describes the synthesis of a compound of the following formula:

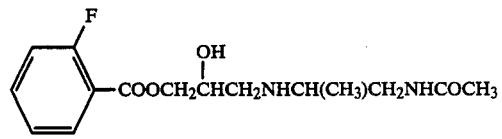

3-[1-methyl-2-(methylcarbonylamino)]ethylamino-2-hydroxypropyl 2-Fluorobenzoate

The procedure of Example II was repeated in all essential details to produce the above compound, except that an equivalent amount of 1-methyl-2-(methylcarbonylamino)ethylamine was substituted for the 1,1-dimethyl-2-(1-morpholinocarbonylamino)ethylamine. The product, which was recovered as a semisolid, had a melting point of 30° C. It was identified by NMR and IR spectroscopy and elemental analysis.

EXAMPLE IV

This example describes the synthesis of a compound of the following formula:

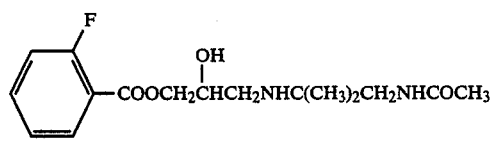

3-[1,1-Dimethyl-2-(methylcarbonylamino)]ethylamino-2-hydroxypropyl 2-Fluorobenzoate The procedure of Example II was repeated in all essential details to produce the above compound except that an equivalent amount of 1,1-dimethyl-2-(methylcarbonylamino)ethylamine was substituted for the 1,1-dimethyl-2-(1-morpholinocarbonylamino)ethylamine. The product, which was recovered as an oil, was identified by NMR and IR spectroscopy and elemental analysis.

EXAMPLE V

This example describes the synthesis of a compound of the following formula:

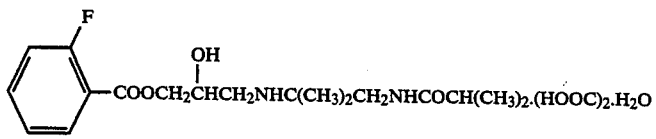

3-[1,1-Dimethyl-2-(isopropylcarbonylamino)]ethylamino-2-hydroxypropyl 2-Fluorobenzoate Oxalate Monohydrate The procedure of Example II was repeated in all essential details to produce the above compound except that an equivalent amount of 1,1-dimethyl-2-isopropylcarbonylaminoethylamine was substituted for the 1,1-dimethyl-2-(1-morpholinocarbonylamino)ethylamine. The product, which was crystallized from isopropanol, had a melting point of 134.5°-137.5° C. and was identified by NMR and IR spectroscopy and elemental analysis.

EXAMPLE VI

This example describes the synthesis of a compound of the following formula:

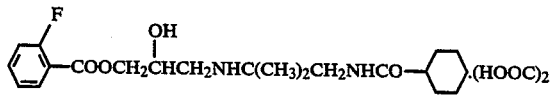

3-[1,1-Dimethyl-2-(cyclohexylcarbonylamino)]ethylamino-2-hydroxypropyl 2-Fluorobenzoate Oxalate The procedure of Example II was repeated in all essential details to produce the above compound except that an equivalent amount of 1,1-dimethyl-2-cyclohexylcarbonylaminoethylamine was substituted for the 1,1-dimethyl-2-(1-morpholinocarbonylamino)ethylamine. The product, which was crystallized from ethyl acetate-propanol, had a melting point of 187°-188° C. and was identified by NMR and IR spectroscopy and elemental analysis.

EXAMPLE VII

This example describes the synthesis of a compound of the following formula:

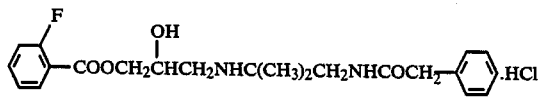

3-[1,1-Dimethyl-2-(benzylcarbonylamino)]ethylamino-2-hydroxypropyl 2-Fluorobenzoate Hydrochloride The procedure of Example II was repeated in all essential details to produce the above compound except that an equivalent amount of 1,1-dimethyl-2-benzylcarbonylaminoethylamine was substituted for the 1,1-dimethyl-2-(-morpholinocarbonylamino)ethylamine. The product, which was crystallized from isopropanol, had a melting point of 145.5°-146.5° C. and was identified by NMR and IR spectroscopy and elemental analysis.

EXAMPLE VIII

This example describes the synthesis of a compound of the following formula:

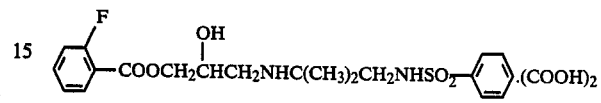

3-[1,1-Dimethyl-2-(phenylsulfonylamino)]ethylamino-2-hydroxypropyl 2-Fluorobenzoate Oxalate The procedure of Example II was repeated in all essential details to produce the above compound except that an equivalent amount of 1,1-dimethyl-2(phenylsulfonylamino)ethylamine was substituted for the 1,1-dimethyl-2-(1-morpholinocarbonylamino)ethylamine. The product, which was crystallized from isopropanol, had a melting point of 152.4°-153° C. and was identified by NMR and IR spectroscopy and elemental analysis.

EXAMPLE IX

This example describes the synthesis of a compound of the following formula:

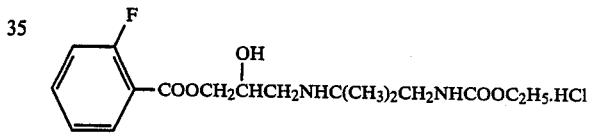

3-[1,1-Dimethyl-2-(ethoxycarbonylamino)]ethylamino-2-hydroxypropyl 2-Fluorobenzoate Hydrochloride The procedure of Example II was repeated in all essential details to produce the above compound except that an equivalent amount of 1,1-dimethyl-2-ethoxycarbonylaminoethylamine was substituted for the 1,1-dimethyl-2-(1-morpholinocarbonylamin)ethylamine. The product, which was crystallized from ethyl acetate, had a melting point of 137° C. and was identifid by NMR and IR spectroscopy and elemental analysis.

EXAMPLE X

This example describes the synthesis of a compound of the following formula

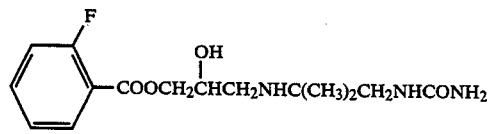

3-[1,1-Dimethyl-2-(aminocarbonylamino)]ethylamino-2-hydroxypropyl 2-Fluorobenzoate The procedure of Example II was repeated in all essential details to produce the above compound except that an equivalent amount of 1,1-dimethyl-2-(aminocarbonylamino)ethylamine was substituted for the 1,1-dimethyl-2-(1-morpholinocarbonylamino)ethylamine. The product which was recrystallized from water, had a melting point of 58°-62° C. and was identified by NMR and IR spectroscopy and elemental analysis.

EXAMPLE XI

This example described the synthesis of a compound of the following formula:

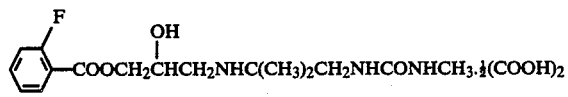

3-[1,1-Dimethyl-2-(methylaminocarbonylamino)]ethylamino-2-hydroxypropyl 2-Fluorobenzoate Hemioxalate The procedure of Example II was repeated in all essential details to produce the above compound except that an equivalent amount of 1,1-dimethyl-2-(methylaminocarbonylamino)ethylamine was substituted for the 1,1-dimethyl-2-(1-morpholinocarbonylamino)ethylamine. The product, which was crystallized from isopropanol, had a melting point of 149.5° C. and was identified by NMR and IR spectroscopy and elemental analysis.

EXAMPLE XII

This example describes the synthesis of a compound of the following formula:

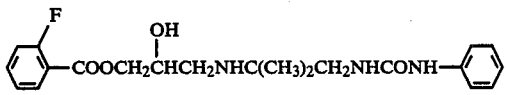

3-[1,1-Dimethyl-2-(phenylaminocarbonylamino)]ethylamino-2-hydroxypropyl 2-Fluorobenzoate The procedure of Example II was repeated in all essential details to produce the above compound except that an equivalent amount of 1,1-dimethyl-2-(phenylaminocarbonylamino)ethylamine was substituted for the 1,1-dimethyl-2-(1-morpholinocarbonylamino)ethylamine. The product, which was recovered as an oil, was identified by NMR and IR spectroscopy and elemental analysis.

EXAMPLE XIII

This example describes the synthesis of a compound of the following formula:

3-[2-(Benzylcarbonylamino)ethyl]amino-2-hydroxypropyl 2-Fluorobenzoate Hydrochloride The procedure of Example I was repeated in all essential details to produce the above compound except that an equivalent amount of 2-(benzylcarbonylamino)ethylamine was substituted for the 2-(isopropylcarbonylamino)ethylamine. The product, which was crystallized from isopropanol, had a melting point of 140.5° C. and was identified by NMR and IR spectroscopy and elemental analysis.

EXAMPLE XIV

This example describes the synthesis of an intermediate amine of the following formula:

1,1-Dimethyl-2-(methylcarbonylamino)ethylamine

A mixture of 26.4 g (0.3 mol) of ethyl acetate and 79.2 g (0.9 mol) of 1,2-diamino-2-methylpropane was heated at 100° C. in a pressure bomb for 36 hours. The reaction mixture was evaporated in vacuo and distilled to give 22.4 g (57.4%) of product; boiling point 100° C./0.1 mmHg. This product was identified by NMR and IR spectroscopy.

EXAMPLE XV

This example describes the synthesis of an intermediate amine of the following formula:

2-(Isopropylcarbonylamino)ethylamine

The procedure of Example XIV was repeated in all essential details to produce the above compound except that equivalent amounts of ethylene diamine and ethyl 2-methylpropionate were substituted for the 1,2-diamino-2-methylpropane and ethyl acetate, respectively. The product, which was recovered as an oil, was identified by NMR and IR spectroscopy and elemental analysis.

EXAMPLE XVI

This example describes the synthesis of an intermediate amine of the following formula:

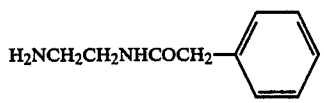

2-(Benzylcarbonylamino)ethylamine

The procedure of Example XIV was repeated in all essential details to produce the above compound except that equivalent amounts of ethylene diamine and ethyl phenylacetate were substituted for the 1,2-diamino-2-methylpropane and ethyl acetate, respectively. The product, which had a melting point of 37°-38° C., was identified by NMR and IR spectroscopy.

EXAMPLE XVII

This example describes the synthesis of an intermediate amine of the following formula:

1-Methyl-2-(methylcarbonylamino)ethylamine

The procedure of Example XIV was repeated in all essential details to produce the above compound except that an equivalent amount of 1,2-diaminopropane was substituted for 1,2-diamino-2-methylpropane. The product, which had a boiling point of 90°-95° C. at 0.1 mmHg, was identified by NMR and IR spectroscopy.

EXAMPLE XVIII

This example describes the synthesis of an intermediate amine of the following formula:

H₂NCH₂CH₂NHCOCH₃

2-(Methylcarbonylamino)ethylamine

The procedure of Example XIV was repeated in all essential details to produce the above compound except that an equivalent amount of ethylene diamine was substituted for 1,2-diamino-2-methylpropane. The product, which had a melting point of 51°–52° C., was identified by NMR and IR spectroscopy.

EXAMPLE IXX

This example describes the synthesis of an intermediate amine of the following formula:

H₂NC(CH₃)₂CH₂NHCOCH(CH₃)₂

1,1-Dimethyl-2-(isopropylcarbonylamino)ethylamine

The procedure of Example XIV was repeated in all essential details to produce the above compound except that an equivalent amount of ethyl 2-methylpropionate was substituted for ethyl acetate. The product, which had a boiling point of 110° C. at 0.1 mmHg, was identified by NMR and IR spectroscopy.

EXAMPLE XX

This example describes the synthesis of an intermediate amine of the following formula:

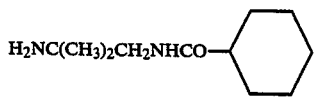

1,1-Dimethyl-2-(cyclohexylcarbonylamino)ethylamine

The procedure of Example XIV was repeated in all essential details to produce the above compound except that an equivalent amount of ethyl cyclohexylcarboxylate was substituted for ethyl acetate. The product, which had a boiling point of 100°–110° C. at 0.1 mmHg, was identified by NMR and IR spectroscopy.

EXAMPLE XXI

This example describes the synthesis of an intermediate amine of the following formula:

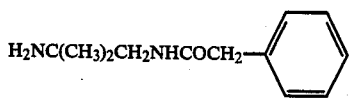

1,1-Dimethyl-2-(benzylcarbonylamino)ethylamine

The procedure of Example XIV was repeated in all essential details to produce the above compound except that an equivalent amount of ethyl phenylacetate was substituted for ethyl acetate. The product, which had a melting point of 46.5° C., was identified by NMR and IR spectroscopy.

EXAMPLE XXII

This example describes the synthesis of an amine of the following formula:

H₂NC(CH₃)₂CH₂NHCOOC₂H₅

1,1-Dimethyl-2-(ethoxycarbonyl)aminoethylamine

To a mixture of 88.2 g (1 mol) of 1,2-diamino-2-methylpropane, 50 ml of triethylamine and 500 ml of diethyl ether was added dropwise to a solution of 27.1 g (0.25 mol) of ethyl chloroformate in 100 mL of ether. The reaction mixture was stirred for 16 hours at 25° C. and filtered. Evaporation of the filtrate to dryness gave 38 g (95%) of product which was identified by NMR and IR spectroscopy.

EXAMPLE XXIII

This example describes the synthesis of an amine of the following formula:

H₂NC(CH₃)₂CH₂NHCONHCH₃

1,1-Dimethyl-2-(methylaminocarbonylamino)ethylamine

A reaction mixture of 5.7 g (1 mol) of methyl isocyanate and 20 ml of pyridine was stirred at 0° C. for 5 minutes and slowly added into a solution of 20 g (0.23 mol) 1,2-diamino-2-methylpropane in 30 ml of pyridine. The reaction mixture was warmed to 20° C. and stirred for 1 hour. Evaporation of the solvent in vacuo gave 11.6 g (90%) of product which was identified by NMR and IR spectroscopy.

EXAMPLE XXIV

This example describes the synthesis of an amine of the following formula:

H₂NC(CH₃)₂CH₂NHCONH₂

1,1-Dimethyl-2-(aminocarbonylamino)ethylamine

The procedure of Example XXIII was repeated in all essential details to produce the above compound except that an equivalent amount of cyanic acid was substituted for methyl isocyanate. The product was recovered as a semi-solid.

Alternatively, the urea of this example was prepared as follows: A mixture of 26.5 g (0.3 mol) of 1,2-diamino-2-methylpropane, and 18 g (0.3 mol) of urea in 150 ml of water was refluxed for 4 hours. The mixture was evaporated in vacuo. The residue was dissolved in chloroform, filtered and evaporated to form a solid which was recrystallized in ethyl acetate to give 15 g of product (38%), m.p. 87°–90° C. The NMR and IR spectra were consistent with the assigned structure.

EXAMPLE XXV

This example describes the synthesis of an amine of the following formula:

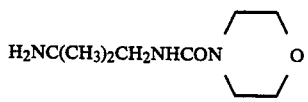

1,1-Dimethyl-2-(1-morpholinocarbonylamino)ethylamine

To 16.2 g (0.1) of N,N'-carbonyldiimidazole in 100 ml of chloroform was added 8.7 g (0.1 mol) of morpholine. The reaction mixture was stirred for 30 minutes at 25° C. and slowly added to a solution of 1,2-diamino-2-methylpropane in 100 ml of chloroform. After stirring for 30 minutes, the reaction was evaporated to dryness and the product was chromatographed; silica gel/ethanol-ethyl ether (1:1) to give 8.74 g (43%) of product. The NMR and IR spectra were consistent with the assigned structure.

EXAMPLE XXVI

This example describes the synthesis of an amine of the following formula:

1,1-Dimethyl-2-(phenylaminocarbonylamino)ethylamine

The procedure of Example XXV was repeated in all essential details to produce the above compound except that an equivalent amount of aniline was substituted for morpholine. The product, which had a melting point of 130.5°–131°, was identified by NMR and IR spectroscopy.

EXAMPLE XXVII

This example describes the synthesis of an amine of the following formula:

H$_2$NCH$_2$CH$_2$NHCONHCH$_3$.HCl 2-(Methylaminocarbonylamino)ethylamine 3.23 g (0.057 mol) of methyl isocynate was added dropwise to a stirring suspension of 5 g (0.057 mol) of acetylethylenediamine in 100 ml of methylene chloride at 10° C. After the addition of methyl isocyanate was completed, 100 ml of anhydrous ether was added to the reaction mixture and stirring was continued for another 30 minutes. A solid having a melting point of 143°–144° C. was collected by filtration. It was dissolved in 50 ml of 15% hydrochloric acid and heated to 80° C. for 4 hours. Removal of the aqueous acid under reduced pressure afforded the product as an oil which was identified by its NMR and IR spectra.

EXAMPLE XVIII

This example describes the synthesis of an amine of the following formula:

2-(Phenylaminocarbonylamino)ethylamine

The procdure of Example XXVII was repeated in all essential details to produce the above compound except that an equivalent amount of phenyl isocyanate was substituted for methyl isocyanate. The product had a melting point of 190.4° C.

EXAMPLE XXIX

This example describes the synthesis of an amine of the following formula:

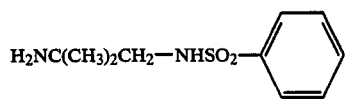

1,1-Dimethyl-2-(phenylsulfonylamino)ethylamine

To a mixture of 14.97 g (0.169 mol) of the 1,2-diamino-2-methylpropane in 300 ml of chloroform and 80 ml pyridine was added 10 g (0.057 mol) of benzenesulfonyl chloride at 0° C. The reaction mixture was stirred at 0° C. for 30 minutes and allowed to reach room temperature. The mixture was evaporated to dryness in vacuo and the residue was partitioned between water and chloroform. Evaporation of the chloroform gave 10.3 g (79%) of semisolid. The product was identified by NMR and IR spectroscopy and elemental analysis.

EXAMPLE XXX

This example describes the synthesis of an amine of the following formula:

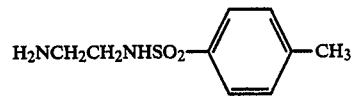

2-(p-Methylphenylsulfonylamino)ethylamine

The procedure of Example XXIX is repeated in all essential details to give the above product except that equivalent amounts of p-toluenesulfonyl chloride and ethylenediamine are substituted for benzenesulfonyl chloride and 1,2-diamino-2-methylpropane, respectively.

EXAMPLE XXXI

This example describes the synthesis of a compound of the following formula:

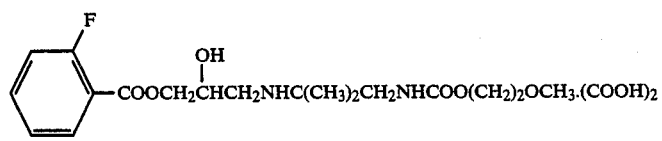

3-[1,1-Dimethyl-2-[(2-methoxy)ethoxycarbonylamino]-]ethylamino-2-hydroxypropyl 2-Fluorobenzoate Oxalate The procedure of Example II was repeated in all essential details to produce the above compound except that an equivalent amount of 1,1-dimethyl-2-[(2-methoxy)ethoxycarbonylamino)ethylamine was substituted for the 1,1-dimethyl-2-(1-morpholinocarbonylamino)ethylamine. The product, which was crystallized from ethyl acetate, had a melting point of 94°-96° C. and was identified by NMR and IR spectroscopy and elemental analysis.

EXAMPLE XXXII

This example describes the synthesis of a compound of the following formula:

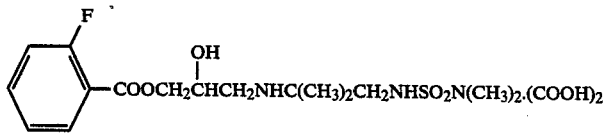

3-[1,1-Dimethyl-2-(dimethylaminosulfonylamino)]ethylamino-2-hydroxypropyl 2-Fluorobenzoate Oxalate The procedure of Example II was repeated in all essential details to produce the above compound except that an equivalent amount of 1,1-dimethyl-2-(dimethylaminosulfonylamino)ethylamine was substituted for the 1,1-dimethyl-2-(1-morpholinocarbonylamino)ethylamine. The product, which was crystallized from acetone-ethylamine, had a melting point of 124°-125° C. and was identified by NMR and IR spectroscopy and elemental analysis.

EXAMPLE XXXIII

This example describes the synthesis of a compound of the following formula:

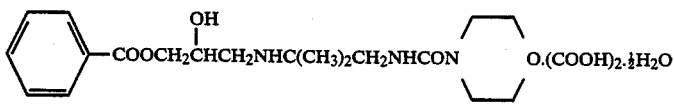

3-[1,1-Dimethyl-2-(1-morpholinocarbonylamino)]ethylamino-2-hydroxypropyl Benzoate Oxalate Hemihydrate The procedure of Example II was repeated in all essential details to produce the above compound except that an equivalent amount of benzoyl chloride was substituted for o-fluorobenzoyl chloride. The product, which was recrystallized from ethyl acetate, had a melting point of 141°-143° C. and was identified by NMR and IR spectroscopy and elemental analysis.

EXAMPLE XXXIV

This example describes the synthesis of a compound of the following formula:

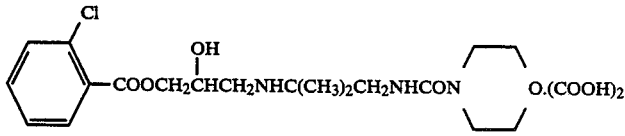

3-[1,1-Dimethyl-2-(1-morpholinocarbonylamino)]ethylamino-2-hydroxypropyl 2-Chlorobenzoate Oxalate The procedure of Example II was repeated in all essential details to produce the above compound except that an equivalent amount of o-chlorobenzoyl chloride was substituted for o-fluorobenzoyl chloride. The product, which was recrystallized from isopropanol-ether, had a melting point of 117°-119° C. and was identified by NMR and IR spectroscopy and elemental analysis.

EXAMPLE XXXV

This sample describes the synthesis of a compound of the following formula:

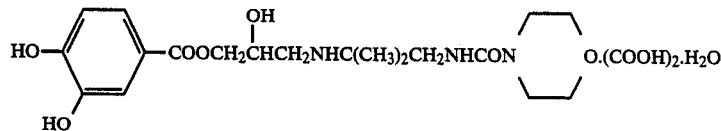

(a) Ethyl 3,4-Dihydroxybenzoate

A mixture which contained 43 g (0.28 mole) of 3,4-dihydroxybenzoic acid, 300 ml of ethanol and 0.5 ml of concentrated $H_2SO_4$ was refluxed for 48 hours. Water was trapped with 3 A molecular sieves. The reaction mixture was evaporated to dryness in vacuo, and partitioned between ether and 5% $NaHCO_3$ solution. The ether layer was evaporated to give 39 g (69%) of solid; m.p. 128°-130° C. The NMR and IR spectra were consistent with the assigned structure.

(b) 3,4-Dibenzyloxybenzoic Acid

To 60 g (0.33 mole) of ethyl 3,4-dihydroxybenzoate in 50 ml of methyl ethyl ketone was added 105.5 g (0.76 mole) of $K_2CO_3$ and 168.8 g (0.76 mole) of benzyl bromide. The mixture was refluxed for 16 hours and filtered. Evaporation of the filtration gave an oil. This oil was mixed with 40 g of KOH, 350 ml of water and 350 ml of methanol and refluxed for 2.5 hours. The methanol was evaporated and the reaction mixture was acidified with concentrated HCl. The precipitate was filtered to give 101 g (92%) of the desired product; m.p. 184°–185° C. The NMR and IR spectra were consistent with the assigned structure.

(c) 3-[1,1-Dimethyl-2-(1-morpholinocarbonylamino)ethyl]amino-2-hydroxypropyl 3,4-Dibenzyloxybenzoate Oxalate Monohydrate To 5 g (15 mmol) of the 3,4-dibenzyloxybenzoic acid in 30 ml of toluene was added 20 g (110 mmol) of thionyl chloride. The reaction mixture was refluxed for 2 hours and evaporated in vacuo to a solid. The solid was dissolved in 20 ml of toluene and added dropwise into a solution of 4.1 g (15 mmol) 3-[1,1-dimethyl-2-(1-morpholinocarbonylamino)]ethylamino-1,2-propandiol in 10 ml of pyridine and 20 ml of toluene. The reaction mixture was stirred for 1 hour at 25° C. and evaporated to dryness. The residue was dissolved in acetone and basified with K₂CO₃. The acetone solution was filtered, evaporated to dryness and the residue was mixed with an equivalent amount of oxalic acid in isopropanol-ether to give 1.5 g (14.3%) of crystalline product, m.p. 162°–163° C. The NMR and IR spectra were consistent with the assigned structure and the elemental analysis was consistent with the empirical formula $C_{35}H_{45}O_{12}N_3$.

(d) 3-[2-[1,1-Dimethyl-2-(1-morpholinocarbonylamino)]ethyl]amino-2-hydroxypropyl 3,4-Dihydroxybenzoate Oxalate Monohydrate A mixture of 1 g of the dibenzyloxybenzoate from the previous experiment, 100 mg of 10% Pd/C and 75 ml of methanol was agitated for 30 minutes under 50 psi of hydrogen. The catalyst was filtered and the filtrate was evaporated to dryness. The residue was crystallized in ethanol-ether to give 0.4 g (54%) of product; m.p. 145°–147° C. The compound was identified by NMR, IR and elemental analysis.

EXAMPLE XXXVI

This example describes the synthesis of a compound of the following formula:

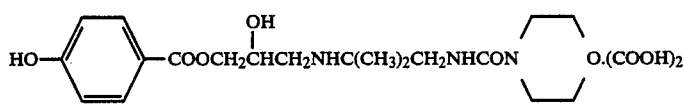

3-[1,1-Dimethyl-2-(1-morpholinocarbonylamino)]ethylamino-2-hydroxypropyl 4-Hydroxybenzoate Oxalate The procedure of Example XXXV was repeated in all essential details to produce the above compound except that an equivalent amount of 4-hydroxybenzoic acid was substituted for the 3,4-dihydroxybenzoic acid. The product, which was crystallized from isopropanol-ethyl acetate-ether, had a melting point of 176°–177° C. and was identified by NMR and IR spectroscopy and elemental analysis.

EXAMPLE XXXVII

This example describes the synthesis of a compound of the following formula:

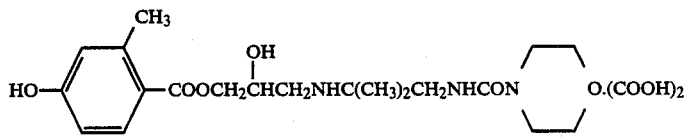

3-[1,1-Dimethyl-2-(1-morpholinocarbonylamino)]ethylamino-2-hydroxypropyl 2-Methyl-4-hydroxybenzoate Oxalate The procedure of Example XXXV was repeated in all essential details to produce the above compound except that an equivalent amount of 2-methyl-4-hydroxybenzoic acid was substituted for the 3,4-dihydroxybenzoic acid. The product, which was recrystallized from isopropanol-ether, had a melting point of 160°–161° C. and was identified by NMR and IR spectroscopy and elemental analysis.

EXAMPLE XXXVIII

This example describes the synthesis of a compound of the following formula:

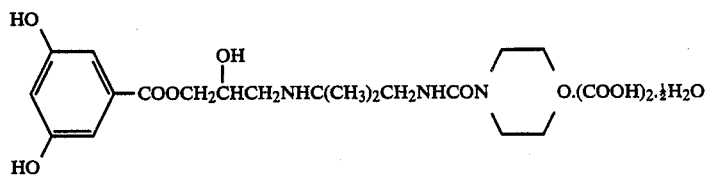

3-[1,1-Dimethyl-2-(1-morpholinocarbonylamino)]ethylamino-2-hydroxypropyl 3,5-Dihydroxybenzoate Oxalate Hemihydrate The procedure of Example XXXV was repeated in all essential details to produce the above compound except that an equivalent amount of 3,5-dihydroxybenzoic acid was substituted for the 3,4-dihydroxybenzoic acid. The product, which was precipitated from isopropanol with ether, was hygroscopic and was identified by NMR and IR spectrocopy and elemental analysis.

EXAMPLE XXXIX

This example describes the synthesis of an amine of the following formula:

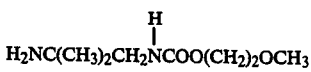

1,1-Dimethyl-2-(methoxyethoxycarbonylamino)ethylamine

To 10 g (62 mmol) of N,N'-carbonyldiimidazole in 100 ml of methylene chloride was added 4.7 g (62 mmol) of 2-methoxyethanol. The reaction mixture was timed at 25° C. for one hour and 10.9 g (124 mmol) of 1,2-diamino-2-methylpropane was added. Stirring was continued for 18 hours and the reaction was evaporated to dryness. The product was chromatographed on silica gel/EtOH:EtOAc (1:1) to give 9.5 g (80.5%) of product. The NMR and IR were consistent with the assigned structure.

EXAMPLE XXXX

This example describes the synthesis of an amine of the following formula:

1,1-Dimethyl-2-[(dimethylamino)sulfonylamino]ethylamine

A mixture of 30.7 g (0.35 mol) of 1,2-diamino-2-methylpropane, 150 ml of ether and 50 ml of triethylamine was cooled to 0° C. and 20 g (0.14 mol) of dimethylsulfamoyl chloride was added slowly. The reaction mixture was stirred for 30 minutes and evaporated to dryness. The residue was mixed with water, basified with K₂CO₃ and evaporated to dryness. Acetone was added and the mixture was filtered. Evaporation of the filtrate gave a solid which was recrystallized from toluene to give 16.5 g (60.3%) of product, mp 77°–78° C. The NMR and IR were consistent with the assigned structure.

EXAMPLE XXXXI

This example describes the synthesis of a compound of the following formula:

2-[(Dimethyaminosulfonylamino]ethylamine Hydrochloride

A solution of 14.3 g (0.1 mole) of dimethylsulfamoyl chloride in 50 ml of methylene chloride was added dropwise to a rapidly stirred solution of 10.2 g (0.1 mole) of acetylethylene diamine and 10.1 g (0.1 mole) of triethylamine in 150 ml of methylene chloride at 25° C. After the addition was completed, the solution was stirred for 30 min and then washed in a separatory funnel with two 100 ml portions of water. The organic phase was separated, and dried over MgSO₄, and then concentrated under reduced pressure to afford N-[2[(dimethylamino)sulfonylamino]ethyl]acetamide as an oil. The N-acetyl group was then removed by treatment of the oil with 100 ml of 15% HCl at 80° C. for 6 h. The solution was concentrated under reduced pressure to provide 12.6 g (73%) of product as an oil. The NMR spectrum was consistent with the assigned structure.

EXAMPLE XXXXII

This example describes the synthesis of a compound of the following formula:

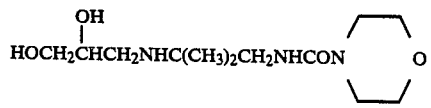

3-[1,1-Dimethyl-2-(morpholinocarbonylamino)ethylamino]-1,2-propanediol

A mixture of 20 g (0.1 mol) of 1,1-dimethyl-2-(1-morpholinocarbonylamino)ethylamine, 7.4 g (0.1 mol) of glycidol and 50 ml of tetrahydrofuran was refluxed for 18 hours. The solvent was evaporated in vacuo to give the product which was identified by NMR and IR.

EXAMPLE XXXXIII

The procedure of Example II is repeated in all essential details to produce the compounds identified in the following table, except that an equivalent amount of the reactant listed in the first column is substituted for o-fluorobenzoyl chloride.

$$ArC(=O)-O-CH_2CHCH_2NH-C(CH_3)_2CH_2NHCON\diagdown O$$ (OH)

| Ar—CCl (O=) | Ar |
|---|---|
| 1-naphthoyl chloride | 1-naphthyl |
| 2-naphthoyl chloride | 2-naphthyl |
| 2-methylbenzoyl chloride | 2-methylphenyl |
| 3-fluorobenzoyl chloride | 3-fluorophenyl |
| 4-fluorobenzoyl chloride | 4-fluorophenyl |
| 3-nitrobenzoyl chloride | 3-nitrophenyl |
| 4-nitrobenzoyl chloride | 4-nitrophenyl |
| 4-methoxybenzoyl chloride | 4-methoxyphenyl |
| 4-cyanobenzoyl chloride | 4-cyanophenyl |
| 2-allyloxybenzoyl chloride | 3-allyloxyphenyl |
| 3-allyloxybenzoyl chloride | 3-allyloxyphenyl |
| 2-n-propyloxybenzoyl chloride | 2-n-propyloxyphenyl |
| 4-formylbenzoyl chloride | 4-formylphenyl |
| 4-benzyloxybenzoyl chloride | 4-benzyloxyphenyl |
| 3,4-benzyloxybenzoyl chloride | 3,4-benzyloxlyphenyl |
| 2-methylbenzoyl chloride | 2-methylphenyl |
| 3-nitrobenzoyl chloride | 3-nitrophenyl |
| 4-nitrobenzoyl chloride | 4-nitrophenyl |
| 2-methyl-4-nitrobenzoyl chloride | 2-methyl-4-nitrophenyl |
| 4-n-butyloxybenzoyl chloride | 4-n-butyloxyphenyl |
| 3,4,5-tribenzyloxybenzoyl chloride | 3,4,5-benzyloxyphenyl |

EXAMPLE XXXXIV

This example describes the synthesis of a compound of the formula:

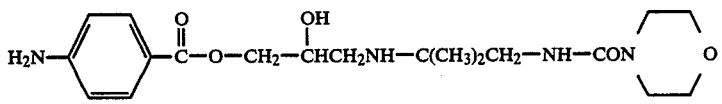

3-[1,1-Dimethyl-2-(1-morpholinocarbonylamino)ethylamino]-2-hydroxypropyl 4-Aminobenzoate To 20 mg of 10% Pd-C in 30 ml of methanol is added 0.00125 moles of methanol is added 0.00125 mole of 3-[1,1-dimethyl-2-(1-morpholinocarbonylamino)ethylamino-2-hydroxypropyl 4-nitrobenzoate prepared in Example XXXXIII. The reaction vessel is kept under 30 psi of hydrogen and agitated for 1 hour. The catalyst is filtered and the methanol evaporated to give the product.

What we claim is:

1. A compound of the formula

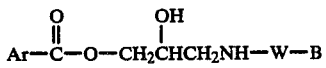

wherein Ar represents a phenyl or naphthyl group which may be unsubstituted or substituted with lower alkyl from 1 to 6 carbon atoms, alkenyl of from 1 to 6 carbon atoms, alkynyl of from 2 to 10 carbon atoms, alkoxy wherein the alkyl group contains from 1 to 6 carbon atoms, halogen, acetamido, amino, nitro, phenoxy, alkylamino of from 1 to 10 carbon atoms, hydroxy, hydroxyalkyl of from 1 to 10 carbon atoms, cyano, arylalkoxy wherein the alkyl group contains from 1 to 6 carbon atoms and the aryl group represents phenyl which may be unsubstituted or substituted with lower alkyl from 1 to 6 carbon atoms, alkenyl of from 2 to 6 carbon atoms, alkynyl of from 2 to 10 carbon atoms, alkoxy wherein the alkyl group contains from 1 to 6 carbon atoms, halogen, acetamido, amino, nitro, phenoxy, alkylamino of from 1 to 10 carbon atoms, hydroxy, hydroxyalkyl of from 1 to 10 carbon atoms, cyano; W represents alkylene of from 1 to 10 carbon atoms; and B represents $-NR_2COR_1$, $-NR_2CONR_1R_3$, $-NR_2SO_2R_1$, $-NR_2SO_2NR_1R_3$, or $-NR_2COOR_1$ wherein $R_1$, $R_2$ and $R_3$ may be the same or different and may be hydrogen, alkyl, alkoxyalkyl, cycloalkyl, alkenyl, alkynyl, phenyl or aralkyl wherein the alkyl group contains from 1 to 6 carbon atoms and the aryl group represents phenyl which may be unsubstituted or substituted with lower alkyl from 1 to 6 carbon atoms, alkenyl of from 2 to 6 carbon atoms, alkynyl of from 2 to 10 carbon atoms, alkoxy wherein the alkyl group contains from 1 to 6 carbon atoms, halogen, acetamido, amino, nitro, phenoxy, alkylamino of from 1 to 10 carbon atoms, hydroxy, hydroxyalkyl of from 1 to 10 carbon atoms, cyano, arylalkoxy wherein the alkyl group contains from 1 to 6 carbon atoms and the aryl group represents phenyl; 1 or 2-thiophenyl, 2, 4 or 5-imidazole, 1- 2- or 1- 3-oxazole or 2 or 3-indole; with the proviso that at least one of $R_1$, $R_2$ and $R_3$ is 1 or 2-thiophenyl, 2, 4 or 5-imidazole, 1- 2- or 1- 3-oxazole or 2 or 3-indole; and except that $R_1$ is not hydrogen when B is $-NR_2SO_2R_1$ or $NR_2COOR_1$; or a pharmaceutically acceptable salt thereof.

2. A compound of the formula

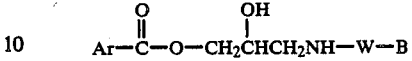

wherein Ar represents phenyl or naphthyl group which may be unsubstituted or substituted with alkyl of from 1 to 6 carbon atoms, alkenyl of from 2 to 6 carbon atoms, alkynyl of from 2 to 10 carbon atoms, alkoxy wherein the alkyl group contains from 1 to 6 carbons atoms, halogen, acetamido, amino, nitro, alkylamino of from 1 to 6 carbon atoms, hydroxy, hydroxyalkyl of from 1 to 6 carbon atoms, cyano or arylalkoxy wherein the alkyl group contains from 1 to 6 carbon atoms and the aryl group is substituted or unsubstituted phenyl; W represents alkylene of from 1 to 10 carbon atoms; and B represents $-NR_2COR_1$, $-NR_2CONR_1R_3$, $-NR_2SO_2R_1$, $-NR_2SO_2NR_1R_3$, OR $-NR_2COOR_1$ wherein $R_1$, $R_2$ and $R_3$ may be the same or different and represent hydrogen, alkyl of from 1 to 6 carbon atoms, alkoxyalkyl wherein the alkyl groups may be the same or different and contain from 1 to 6 carbon atoms, cycloalkyl of from 3 to 8 carbon atoms, alkenyl of from 2 to 6 carbon atoms, alkynyl of from 2 to 6 carbon atoms, phenyl which may be unsubstituted or substituted with alkyl of 1 to 6 carbon atoms; 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; aralkyl wherein the alkyl group contains from 1 to 6 carbon atoms and the aryl group represents phenyl unsubstituted or substituted with alkyl of from 1 to 6 carbon atoms; and except that $R_1$ is not hydrogen when B is $-NR_2SO_2R_1$ or $-NR_2COOR_1$; or a pharmaceutically acceptable salt thereof.

3. A compound of the formula

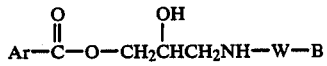

wherein Ar represents phenyl which is unsubstituted or substituted with alkyl of from 1 to 6 carbon atoms, alkoxy wherein the alkyl group contains from 1 to 4 carbon atoms, halogen, hydroxy, nitro, amino, phenoxy, or benzyloxy; W represents alkylene of from 1 to 6 carbon atoms; and B represents $-NR_2COR_1$, $-NR_2CONR_1R_3$, $-NR_2SO_2R_1$, $-NR_2SO_2NR_1R_3$, or $-NR_2COOR_1$ wherein $R_1$, $R_2$ and $R_3$ may be the same or different and represent hydrogen, alkyl of from 1 to 6 carbon atoms, alkoxyalkyl wherein the alkyl groups may be the same or different and contain from 1 to 6 carbon atoms, cycloalkyl of from 3 to 8 carbon atoms, a phenyl group which may be unsubstituted or substituted with lower alkyl of from 1 to 10 carbon atoms, alkenyl of from 2 to 10 carbon atoms, alkynyl of from 2 to 10 carbon atoms, alkoxy wherein the alkyl group contains from 1 to 10 carbon atoms, halogen, acetamido, amino, nitro, alkylamino of from 1 to 10 carbon atoms, hydroxy, hydroxyalkyl of from 1 to 10 carbon atoms, cyano, arylalkoxy wherein the alkyl group contains from 1 to 6 carbon atoms; or 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when B is —$NR_2SO_2R_1$ or —$NR_2COOR_1$; or a pharmaceutically acceptable salt thereof.

4. A compound of the formula

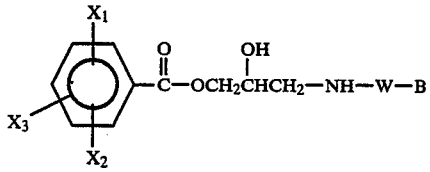

wherein $X_1$, $X_2$ and $X_3$ may be the same or different and represent hydrogen, halogen, hydroxy, hydroxyalkyl of from 1 to 6 carbon atoms, nitro, amino, alkyl of from 1 to 6 carbon atoms, phenoxy, benzyloxy, or alkoxy wherein the alkyl group contains from 1 to 4 carbon atoms; W represents alkylene of from 1 to 6 carbon atoms; and B represents —$NR_2COR_1$, —$NR_2CONR_1R_3$, —$NR_2SO_2R_1$—$NR_2SO_2NR_1R_3$, or —$NR_2COOR_1$ wherein $R_1$, $R_2$, and $R_3$ may be the same or different and represent, hydrogen, alkyl of from 1 to 6 carbon atoms, alkoxyalkyl wherein the alkyl groups may be the same or different and contain from 1 to 6 carbon atoms, cycloalkyl of from 3 to 8 carbon atoms, phenyl, 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when B is —$NR_2SO_2R_1$ or —$NR_2COOR_1$; or a pharmaceutically acceptable salt thereof.

5. A compound according to claim 1 of the formula

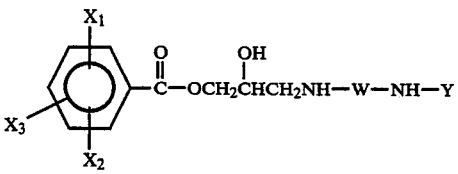

wherein $X_1$, $X_2$ and $X_3$ may be the same or different and represent hydrogen, halogen, hydroxy, hydroxyalkyl of from 1 to 6 carbon atoms, nitro, amino, benzyloxy, phenoxy, alkyl containing from 1 to 6 carbon atoms, or alkoxy wherein the alkyl group contains from 1 to 6 carbon atoms; W represents alkylene of from 1 to 6 carbon atoms; and Y is —$COR_1$, —$CONR_1R_3$, —$SO_2R_1$, —$SO_2NR_1R_3$, or —$COOR_1$, wherein $R_1$ and $R_3$ may be the same or different and may be hydrogen, alkyl containing from 1 to 6 carbon atoms, alkoxyalkyl wherein the alkyl groups may be the same or different and contain from 1 to 6 carbon atoms, phenyl, which may be unsubstituted or substituted with alkyl of from 1 to 6 carbon atoms, alkoxy wherein the alkyl group contains from 1 to 4 carbon atoms, halogen, hydroxy, nitro, amino, phenoxy, benzyloxy, 1 or 2-thiophenyl, 2, 4 or 5-imidazole, 1- 2- or 1- 3-oxazole or 2 or 3-indole; aralkyl wherein the alkyl group contains from 1 to 6 carbon atoms and the aryl group represents phenyl which may be unsubstituted or substituted with alkyl of from 1 to 6 carbon atoms, alkoxy wherein the alkyl group contains from 1 to 4 carbon atoms, halogen, hydroxy, nitro, amino, phenoxy, or benzyloxy with the proviso that at least one of $R_1$ or $R_3$ is 1 or 2-thiophenyl, 2, 4 or 5-imidazole, 1- 2- or 1- 3-oxazole or 2 or 3-indole; and except that $R_1$ is not hydrogen when Y is —$SO_2R_1$ or —$COOR_1$; or a pharmaceutically acceptable salt thereof.

6. A compound according to claim 1 of the formula

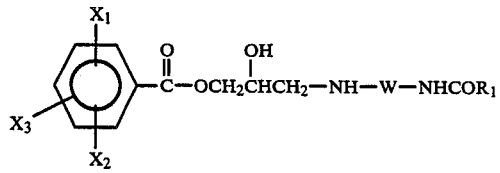

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ represents 1 or 2-thiophenyl, 2, 4 or 5-imidazole, 1- 2- or 1- 3-oxazole or 2 or 3-indole; or a pharmaceutically acceptable salt thereof.

7. A compound according to claim 1 of the formula

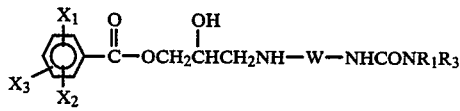

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ and $R_3$ may be the same or different and represent hydrogen, alkyl of from 1 to 6 carbon atoms, alkoxyalkyl wherein the alkyl groups may be the same or different and contain from 1 to 4 carbon atoms, cycloalkyl of from 3 to 8 carbon atoms, phenyl, or benzyl; 1 or 2-thiophenyl, 2, 4 or 5-imidazole, 1- 2- or 1- 3-oxazole or 2 or 3-indole; with the proviso that at least one of $R_1$ or $R_3$ is 1 or 2-thiophenyl, 2, 4 or 5-imidazole, 1- 2- or 1- 3-oxazole or 2 or 3-indole; or a pharmaceutically acceptable salt thereof.

8. A compound according to claim 1 of the formula

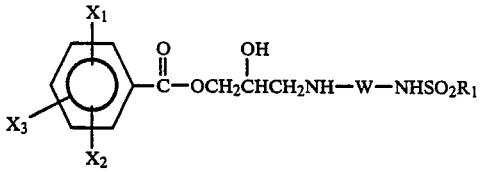

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ represents 1 or 2-thiophenyl, 2, 4 or 5-imidazole, 1- 2- or 1- 3-oxazole or 2 or 3-indole; or a pharmaceutically acceptable salt thereof.

9. A compound according to claim 1 of the formula

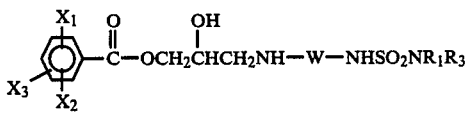

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ and $R_3$ may be the same or different and represent hydrogen, alkyl of from 1 to 6 carbon atoms, alkoxyalkyl wherein the alkyl groups may be the same or different and contain from 1 to 4 carbon atoms, cycloalkyl of from 3 to 8 carbon atoms, phenyl, benzyl, 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2- or 3-indole; or a pharmaceutically acceptable salt thereof.

10. A compound according to claim 1 of the formula

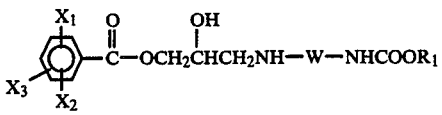

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ represents 1 or 2-thiophenyl, 2, 4 or 5-imidazole, 1- 2- or 1- 3-oxazole or 2 or 3-indole; or a pharmaceutically acceptable salt thereof.

11. A method for the treatment or prophylaxis of cardiac disorders in a mammal comprising administering to such animal a short-acting beta-blocking compound of the formula

wherein Ar represents phenyl or naphthyl group which may be unsubstituted or substituted with lower alkyl of from 1 to 10 carbon atoms, alkenyl of from 2 to 10 carbon atoms, alkynyl of from 2 to 10 carbon atoms, alkoxy wherein the alkyl group contains from 1 to 10 carbon atoms, halogen, acetamido, amino, nitro, alkylamino of from 1 to 10 carbon atoms, hydroxy, hydroxyalkyl of from 1 to 10 carbon atoms, cyano, arylalkoxy wherein the alkyl group contains from 1 to 6 carbon atoms and the aryl group represents substituted or unsubstituted phenyl and groups of the formula

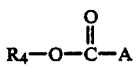

wherein $R_4$ is lower alkyl, aryl or aralkyl and A is a direct bond, alkylene of from 1 to 10 carbon atoms or alkenylene of from 2 to 10 carbon atoms; W represents alkylene of from 1 to 10 carbon atoms; and B represents $-NR_2COR_1$, $-NR_2CONR_1R_3$, $-NR_2SO_2R_1$, $-NR_2SO_2NR_1R_3$, or $-NR_2COOR_1$ wherein $R_1$, $R_2$ and $R_3$ may be the same or different and may be hydrogen, alkyl, alkoxyalkyl, cycloalkyl, alkenyl, alkynyl, aryl, or aralkyl wherein the alkyl group contains from 1 to 6 carbon atoms and the aryl group represents phenyl, benzyl, phenethyl 3,4-dimethoxyphenethyl; or 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; and except that $R_1$ is not hydrogen when B is $-NR_2SO_2R_1$ or $-NR_2COOR_1$, or a pharmaceutically acceptable salt thereof.

12. The method of claim 11 wherein the compound is of the formula

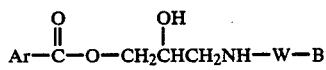

wherein Ar represents an aromatic group which may be unsubstituted or substituted with alkyl of from 1 to 6 carbon atoms, alkenyl of from 2 to 6 carbon atoms, alkynyl of from 2 to 10 carbon atoms, alkoxy wherein the alkyl group contains from 1 to 6 carbon atoms, halogen, acetamido, amino, nitro, alkylamino of from 1 to 6 carbon atoms, hydroxy, hydroxyalkyl of from 1 to 6 carbon atoms, cyano or arylalkoxy wherein the alkyl group contains from 1 to 6 carbon atoms and the aryl group is phenyl; which may be unsubstituted or substituted with alkyl of from 1 to 6 carbon atoms, alkoxy wherein the alkyl group contains from 1 to 4 carbon atoms, halogen, hydroxy, nitro, amino, phenoxy, or benzyloxy; W represents alkylene of from 1 to 10 carbon atoms; and B represents $-NR_2COR_1$, $-NR_2CONR_1R_3$, $-NR_2SO_2R_1$, $-NR_2SO_2NR_1R_3$, or $-NR_2COOR_1$ wherein $R_1$, $R_2$ and $R_3$ may be the same or different and represent hydrogen, alkyl of from 1 to 6 carbon atoms, alkoxyalkyl wherein the alkyl groups may be the same or different and contain from 1 to 6 carbon atoms, cycloalkyl of from 3 to 8 carbon atoms, alkoxyalkyl wherein the alkyl groups may be the same or different and contain from 1 to 6 carbon atoms, cycloalkyl of from 3 to 8 carbon atoms, alkenyl of from 2 to 6 carbon atoms, alkynyl of from 2 to 6 carbon atoms, aralkyl wherein the alkyl group contains from 1 to 6 carbon atoms and the aryl group represents a substituted or unsubstituted aromatic group of from 2 to 10 carbon atoms wherein the substituent groups may be alkyl of from 1 to 6 carbon atoms; phenyl, 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when B is $-NR_2SO_2R_1$ or $-NR_2COOR_1$; or a pharmaceutically acceptable salt thereof.

13. The method of claim 11 wherein the compound is of the formula

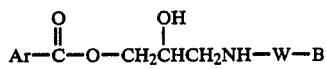

wherein Ar represents phenyl which is unsubstituted or substituted with alkyl of from 1 to 6 carbon atoms, alkoxy wherein the alkyl group contains from 1 to 4 carbon atoms, halogen, hydroxy, nitro, amino, phenoxy, or benzyloxy; W represents alkylene of from 1 to 6 carbon atoms; and B represents $-NR_2COR_1$, $-NR_2CONR_1R_3$, $-NR_2SO_2R_1$, $-NR_2SO_2NR_1R_3$, or $-NR_2COOR_1$, wherein $R_1$, $R_2$ and $R_3$ may be the same or different and represent hydrogen, alkyl of from 1 to 6 carbon atoms, alkoxyalkyl wherein the alkyl groups may be the same or different and contain from 1 to 6 carbon atoms, cycloalkyl of from 3 to 8 carbon atoms, a substituted or unsubstituted aryl group of from 5 to 6 carbon atoms wherein the substituent group may be alkyl of from 1 to 6 carbon atoms; 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-imdole; except that $R_1$ is not hydrogen when B is $-NR_2SO_2R_1$ or $-NR_2COOR_1$; or a pharmaceutically acceptable salt thereof.

14. The method of claim 11 wherein the compound is of the formula

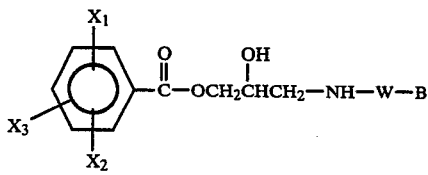

wherein $X_1$, $X_2$ and $X_3$ may be the same or different and represent hydrogen, halogen, hydroxy, hydroxyalkyl of from 1 to 6 carbon atoms, nitro, amino, alkyl of from 1 to 6 carbon atoms, phenoxy, benzyloxy, or alkoxy wherein the alkyl group contains from 1 to 4 carbon atoms; W represents alkylene of from 1 to 6 carbon atoms; and B represents $-NR_2COR_1$, $-NR_2CONR_1R_3$, $-NR_2SO_2R_1$, $-NR_2SO_2NR_1R_3$, or $-NR_2COOR_1$ wherein $R_1$, $R_2$, and $R_3$ may be the same or different and represent, alkyl of from 1 to 6 carbon atoms, alkoxyalkyl wherein the alkyl groups may be the same or different and contain from 1 to 6 carbon atoms, cycloalkyl of from 3 to 8 carbon atoms, phenyl, benzyl, 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when B is $-NR_2SO_2R_1$ or $-NR_2COOR_1$; or a pharmaceutically acceptable salt thereof.

15. The method of claim 11 wherein the compound is of the formula

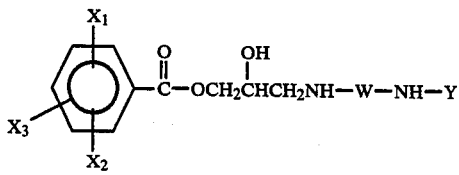

wherein $X_1$, $X_2$ and $X_3$ may be the same or different and represent hydrogen, halogen, hydroxy, hydroxyalkyl of from 1 to 6 carbon atoms, nitro, amino, benzyloxy, phenoxy, alkyl containing from 1 to 6 carbon atoms, or alkoxy wherein the alkyl group contains from 1 to 6 carbon atoms; W represents ethylene, 1-methylene, or 1,1-dimethylethylene, and Y is $-COR_1$, $-CONR_1R_3$, $-SO_2R_1$, $-SO_2NR_1R_3$, or $-COOR_1$, wherein $R_1$ and $R_3$ may be the same or different and may be hydrogen, alkyl containing from 1 to 6 carbon atoms, alkoxyalkyl wherein the alkyl groups may be the same or different and contain from 1 to 6 carbon atoms, phenyl, which may be unsubstituted or substituted with alkyl of from 1 to 6 carbon atoms, alkoxy wherein the alkyl group contains from 1 to 4 carbon atoms, halogen, hydroxy, nitro, amino, phenoxy, or benzyloxy; aralkyl wherein the alkyl group contains from 1 to 6 carbon atoms and the aryl group represents substituted or unsubstituted phenyl or a benzyl, phenethyl, 3,4-dimethoxyphenethyl group; or 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when Y is $-SO_2R_1$ or $-COOR_1$; or a pharmaceutically acceptable salt thereof.

16. The method of claim 11 wherein the compound is of the formula

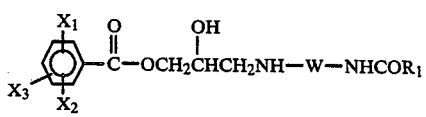

wherein $X_1$, $X_2$ and $X_3$ may be the same or different and represent 1 or 2-thiophenyl, 2, 4 or 5-imidazole, 1- 2- or 1- 3-oxazole or 2 or 3-indole; or a pharmaceutically acceptable salt thereof.

17. The method of claim 11 wherein the compound is of the formula

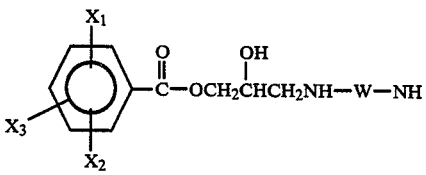

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ and $R_3$ may be the same or different and represent hydrogen, alkyl of from 1 to 6 carbon atoms, alkoxyalkyl wherein the alkyl groups may be the same or different and contain from 1 to 4 carbon atoms, cycloalkyl of from 3 to 8 carbon atoms, phenyl, or benzyl, 1 or 2-thiophenyd, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; or a pharmaceutically acceptable salt thereof.

18. The method of claim 11 wherein the compound is of the formula

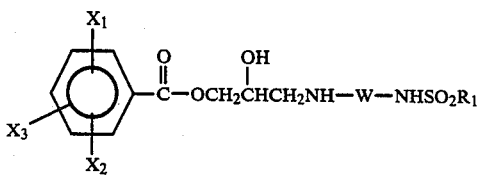

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ represents 1 or 2-thiophenyl, 2, 4 or 5-imidazole, 1- 2- or 1- 3-oxazole or 2 or 3-indole; or a pharmaceutically acceptable salt thereof.

19. The method of claim 11 wherein the compound is of the formula

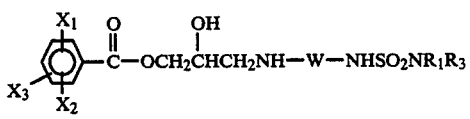

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ and $R_3$ may be the same or different and represent hydrogen, alkyl of from 1 to 6 carbon atoms, alkoxyalkyl wherein the alkyl groups may be the same or different and contain from 1 to 4 carbon atoms, cycloalkyl of from 3 to 8 carbon atoms, phenyl, benzyl, 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; or a pharmaceutically acceptable salt thereof.

20. The method of claim 11 wherein the compound is of the formula

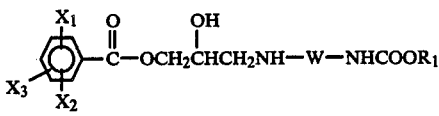

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ represents 1 or 2-thiophenyl, 2, 4 or 5-imidazole, 1- 2- or 1- 3-oxazole or 2 or 3-indole; or a pharmaceutically acceptable salt thereof.

21. A method according to claim 11 wherein the compound is administered parenterally.

22. A method according to claim 21 wherein the compound is administered by intravenous injection or intravenous infusion at a dosage rate of from 0.001 to about 100 mg. of compound per kg. of body weight of said mammal per hour.

23. A method of treating glaucoma or lowering intraocular pressure in a mammal, which comprises topically applying to the eye of said mammal an intraocular pressure-lowering effective amount of a compound of the formula

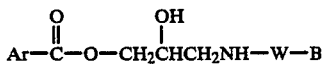

wherein Ar represents a phenyl or naphthyl group which may be unsubstituted or substituted with lower alkyl of from 1 to 10 carbon atoms, alkenyl of from 2 to 10 carbon atoms, alkynyl of from 2 to 10 carbon atoms, alkoxy wherein the alkyl group contains from 1 to 10 carbon atoms, halogen, acetamido, amino, nitro, alkylamino, of from 1 to 10 carbon atoms, hydroxy, hydroxyalkyl of from 1 to 10 carbon atoms, cyano, arylalkoxy wherein the alkyl group contains from 1 to 6 carbon atoms and the aryl group represents substituted or unsubstituted phenyl; W represents alkylene of from 1 to 10 carbon atoms; and B represents —$NR_2COR_1$, —$NR_2CONR_1R_3$, —$NR_2SO_2R_1$, —$NR_2SO_2NR_1R_3$, or —$NR_2COOR_1$ wherein $R_1$, $R_2$ and $R_3$ may be the same or different and may be hydrogen, alkyl, alkoxyalkyl, cycloalkyl, alkenyl, alkynyl, aryl, or aralkyl, 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when B is —$NR_2SO_2R_1$ or —$NR_2COOR_1$; or a pharmaceutically acceptable salt thereof.

24. The method of claim 23 wherein the compound is of the formula

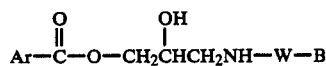

wherein Ar represents an aromatic group which may be unsubstituted or substituted with alkyl of from 1 to 6 carbon atoms, alkenyl of from 2 to 6 carbon atoms, alkynyl of from 2 to 10 carbon atoms, alkoxy wherein the alkyl group contains from 1 to 6 carbon atoms, halogen, acetamido, amino, nitro, alkylamino of from 1 to 6 carbon atoms, hydroxy, hydroxyalkyl of from 1 to 6 carbon atoms, cyano or arylalkoxy wherein the alkyl group contains from 1 to 6 carbon atoms and the aryl group is phenyl which may be unsubstituted or substituted with alkyl of from 1 to 6 carbon atoms, alkoxy wherein the alkyl group contains from 1 to 4 carbon atoms, halogen, hydroxy, nitro, amino, phenoxy or benzyloxy; W represents alkylene of from 1 to 10 carbon atoms; and B represents —$NR_2COR_1$, —$NR_2CONR_1R_3$, —$NR_2SO_2R_1$, —$NR_2SO_2NR_1R_3$, or —$NR_2COOR_1$ wherein $R_1$, $R_2$ and $R_3$ may be the same or different and represent hydrogen, alkyl of from 1 to 6 carbon atoms, alkoxyalkyl wherein the alkyl groups may be the same or different and contain from 1 to 6 carbon atoms, cycloalkyl of from 3 to 8 carbon atoms, alkenyl of from 2 to 6 carbon atoms, alkynyl of from 2 to 6 carbon atoms, aralkyl wherein the alkyl group contains from 1 to 6 carbon atoms and the aryl group represents phenyl, benzyl, phenethyl, or 3,4-dimethoxyphenethyl; 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when B is —$NR_2SO_2R_1$ or —$NR_2COOR_1$; or a pharmaceutically acceptable salt thereof.

25. The method of claim 23 wherein the compound is of the formula

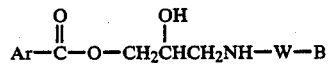

wherein Ar represents phenyl which is unsubstituted or substituted with alkyl of from 1 to 6 carbon atoms, alkoxy wherein the alkyl group contains from 1 to 4 carbon toms, halogen, hydroxy, nitro, amino, phenoxy, or benzyloxy; W represents alkylene of from 1 to 6 carbon atoms; and B represents —$NR_2COR_1$, —$NR_2CONR_1R_3$, —$NR_2SO_2R_1$, —$NR_2SO_2NR_1R_3$, or —$NR_2COOR_1$, wherein $R_1$, $R_2$ and $R_3$ may be the same or different and represent hydrogen, alkyl of from 1 to 6 carbon atoms, alkoxyalkyl wherein the alkyl groups may be the same or different and contain from 1 to 6 carbon atoms, cycloalkyl of from 3 to 8 carbon atoms, a substituted or unsubstituted aryl group of from 5 to 6 carbon atoms wherein the substituent groups may be alkyl of from 1 to 6 carbon atoms; 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when B is —$NR_2SO_2R_1$ or —$NR_2COOR_1$; or a pharmaceutically acceptable salt thereof.

26. The method of claim 23 wherein the compound is of the formula

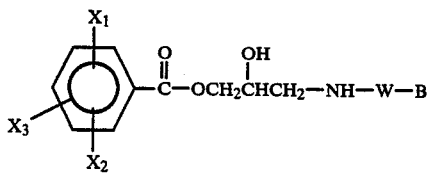

wherein $X_1$, $X_2$ and $X_3$ may be the same or different and represent hydrogen, halogen, hydroxy, hydroxyalkyl of from 1 to 6 carbon atoms, nitro, amino, alkyl of from 1 to 6 carbon atoms, phenoxy benzyloxy, or alkoxy wherein the alkyl group contains from 1 to 4 carbon atoms; W represents alkylene of from 1 to 6 carbon atoms; and B represents —$NR_2COR_1$, —$NR_2CONR_1R_3$, —$NR_2SO_2R_1$, —$NR_2SO_2NR_1R_3$, or —$NR_2COOR_1$ wherein $R_1$, $R_2$, and $R_3$ may be the same or different and represent alkyl of from 1 to 6 carbon atoms, alkoxyalkyl wherein the alkyl groups may be the same or different and contain from 1 to 6 carbon atoms, cycloalkyl of from 3 to 8 carbon atoms, phenyl, benzyl, 1 or 2-thiophenyl, 2, 4 or 5-imidazole, 1- 2- or 1- 3- oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when B is —$NR_2SO_2R_1$ or —$NR_2COOR_1$, or a pharmaceutically acceptable salt thereof.

27. The method of claim 23 wherein the compound is of the formula

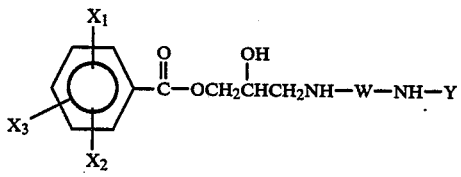

wherein $X_1$, $X_2$ and $X_3$ may be the same or different and represent hydrogen, halogen, hydroxy, hydroxyalkyl of from 1 to 6 carbon atoms, nitro, amino, benzyloxy, phenoxy, alkyl containing from 1 to 6 carbon atoms, or alkoxy wherein the alkyl group contains from 1 to 6 carbon atoms; W represents ethylene, 1-methylethylene, or 1,1-dimethylethylene, and Y is —$COR_1$, —$CONR_1R_3$, —$SO_2R_1$, —$SO_2NR_1R_3$, or —$COOR_1$, wherein $R_1$ and $R_3$ may be the same or different and may be hydrogen, alkyl containing from 1 to 6 carbon atoms, alkoxyalkyl wherein the alkyl groups may be the same or different and contain from 1 to 6 carbon atoms, phenyl, which may be unsubstituted or substituted with alkyl of from 1 to 6 carbon atoms, alkoxy wherein the alkyl group contains from 1 to 4 carbon atoms, halogen, hydroxy, nitro, amino, phenoxy, or benzyloxy; aralkyl wherein the alkyl group contains from 1 to 6 carbon atoms and the aryl group represents phenyl which may be unsubstituted or substituted with alkyl of from 1 to 6 carbon atoms, alkoxy wherein the alkyl group contains from 1 to 4 carbon atoms, halogen, hydroxy, nitro, amino, phenoxy; or 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when Y is —$SO_2R_1$ or —$COOR_1$; or a pharmaceutically acceptable salt thereof.

28. The method of claim 23 wherein the compound is of the formula

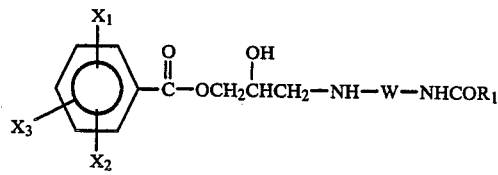

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ represents 1 or 2-thiophenyl, 2, 4 or 5-imidazole, 1- 2- or - 3-oxazole or 2 or 3-indole; or a pharmaceutically acceptable salt thereof.

29. The method of claim 23 wherein the compound is of the formula

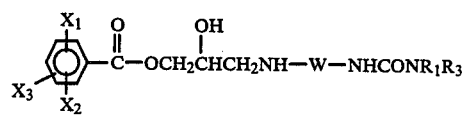

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ and $R_3$ may be the same or different and represent hydrogen, alkyl of from 1 to 6 carbon atoms, alkoxyalkyl wherein the alkyl groups may be the same or different and contain from 1 to 4 carbon atoms, cycloalkyl of from 3 to 8 carbon atoms, phenyl, or benzyl, 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; or a pharmaceutically acceptable salt thereof.

30. The method of claim 23 wherein the compound is of the formula

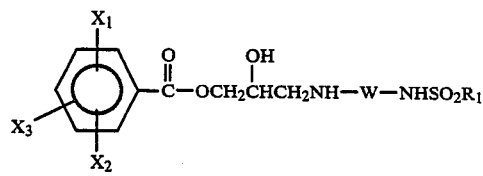

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ represents 1 or 2-thiophenyl, 2, 4 or 5-imidazole, 1- 2- or 1- 3-oxazole or 2 or 3-indole; or a pyrrolidine, piperidine, piperazine, morpholine or thiomorpholine ring, or a pharmaceutically acceptable salt thereof.

31. The method of claim 23 wherein the compound is of the formula

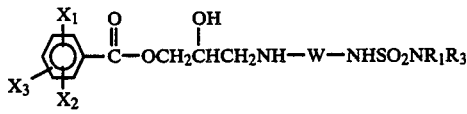

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ and $R_3$ may be the same or different and represent hydrogen, alkyl of from 1 to 6 carbon atoms, alkoxyalkyl wherein the alkyl groups may be the same or different and contain from 1 to 4 carbon atoms, cycloalkyl of from 3 to 8 carbon atoms, phenyl, benzyl, 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; or a pharmaceutically acceptable salt thereof.

32. The method of claim 23 wherein the compound is of the formula

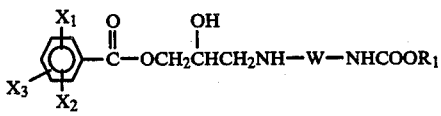

wherein $X_1$, $X_2$ and $X_3$ may be the same or different and represent hydrogen, halogen, hydroxy, nitro, amino, alkyl of from 1 to 4 carbon atoms, or benzyloxy; W represents alkylene of from 1 to 6 carbon atoms; and $R_1$ represents 1 or 2-thiophenyl, 2, 4 or 5-imidazole, 1- 2- or 1- 3-oxazole or 2 or 3-indole; or a pharmaceutically acceptable salt thereof.

33. A method for the treatment or prophylaxis of cardiac disorders comprising administering to a patient in need of such treatment a therapeutically effective amount of a beta-blocking compound of the formula

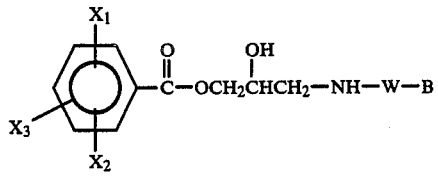

wherein $X_1$, $X_2$ and $X_3$ may be the same or different and represent hydrogen, halogen, hydroxy, hydroxyalkyl of from 1 to 6 carbon atoms, nitro, amino, alkyl of from 1 to 6 carbon atoms, phenoxy, benzyloxy, or alkoxy wherein the alkyl group contains from 1 to 4 carbon atoms; W represents alkylene of from 1 to 6 carbon atoms; and B represents —$NR_2COR_1$, —$NR_2CONR_1R_3$, —$NR_2SO_2R_1$, —$NR_2SO_2NR_1R_3$, or —$NR_2COOR_1$ wherein $R_1$, $R_2$, and $R_3$ may be the same or different and represent hydrogen, alkyl of from 1 to 6 carbon atoms, alkoxyalkyl wherein the alkyl groups may be the same or different and contain from 1 to 6 carbon atoms, cycloalkyl of from 3 to 8 carbon atoms, phenyl or benzyl, 1 or 2-thiophenyl, 2, 4 or 5-imidazole, 1- 2- or 1- 3-oxazole or 2 or 3-indole; with the proviso that at least one of $R_1$, $R_2$ or $R_3$ is 1 or 2-thiophenyl, 2, 4 or 5-imidazole, 1- 2- or 1- 3-oxazole or 2 or 3-indole; except that $R_1$ is not hydrogen when B is —$NR_2SO_2R_1$ or —$NR_2COOR_1$; or a pharmaceutically acceptable salt thereof.

* * * * *